US011766667B2

(12) United States Patent
Onozuka et al.

(10) Patent No.: US 11,766,667 B2
(45) Date of Patent: Sep. 26, 2023

(54) ZEOLITE CATALYST AND METHOD FOR PRODUCING LOWER OLEFIN

(71) Applicants: Mitsubishi Chemical Corporation, Tokyo (JP); JAPAN TECHNOLOGICAL RESEARCH ASSOCIATION OF ARTIFICIAL PHOTOSYNTHETIC CHEMICAL PROCESS, Tokyo (JP)

(72) Inventors: Hiroaki Onozuka, Chiyoda-ku (JP); Masahiro Hara, Chiyoda-ku (JP); Masato Yoshioka, Meguro-ku (JP); Toshiyuki Yokoi, Meguro-ku (JP)

(73) Assignees: Mitsubishi Chemical Corporation, Tokyo (JP); JAPAN TECHNOLOGICAL RESEARCH ASSOCIATION OF ARTIFICIAL PHOTOSYNTHETIC CHEMICAL PROCESS, Tokyo (JP)

( * ) Notice: Subject to any disclaimer, the term of this patent is extended or adjusted under 35 U.S.C. 154(b) by 47 days.

(21) Appl. No.: 17/195,087

(22) Filed: Mar. 8, 2021

(65) Prior Publication Data
US 2021/0213433 A1 Jul. 15, 2021

Related U.S. Application Data

(63) Continuation of application No. 16/595,539, filed on Oct. 8, 2019, now abandoned, which is a continuation
(Continued)

(30) Foreign Application Priority Data

Nov. 25, 2015 (JP) ................. 2015-229994

(51) Int. Cl.
*B01J 29/70* (2006.01)
*B01D 53/00* (2006.01)
*C07C 11/06* (2006.01)
*C07C 11/04* (2006.01)
*C07C 11/08* (2006.01)
(Continued)

(52) U.S. Cl.
CPC .............. *B01J 29/70* (2013.01); *B01D 53/00* (2013.01); *B01D 53/9418* (2013.01); *B01J 20/18* (2013.01); *B01J 20/28002* (2013.01); *B01J 20/28004* (2013.01); *B01J 20/28011* (2013.01); *B01J 29/48* (2013.01); *B01J 29/72* (2013.01); *B01J 29/76* (2013.01); *B01J 35/002* (2013.01); *B01J 35/023* (2013.01); *B01J 37/04* (2013.01); *C01B 39/48* (2013.01); *C07C 1/20* (2013.01); *C07C 11/04* (2013.01); *C07C 11/06* (2013.01); *C07C 11/08* (2013.01); *B01D 2255/104* (2013.01); *B01D 2255/106* (2013.01); *B01D 2255/1021* (2013.01); *B01D 2255/1023* (2013.01); *B01D 2255/1028* (2013.01); *B01D 2255/2063* (2013.01); *B01D 2255/2065* (2013.01); *B01D 2255/2066* (2013.01); *B01D 2255/20707* (2013.01); *B01D 2255/20715* (2013.01); *B01D 2255/20738* (2013.01); *B01D 2255/20746* (2013.01); *B01D 2255/20761* (2013.01); *B01D 2255/50* (2013.01); *B01D 2255/9202* (2013.01); *B01D 2255/9205* (2013.01); *B01D 2255/9207* (2013.01); *C01B 39/04* (2013.01); *C07C 2529/70* (2013.01);
(Continued)

(58) Field of Classification Search
CPC ................ B01D 53/00; B01D 53/9418; B01D 2255/1023; B01D 2255/20761; B01D 2255/20746; B01D 2255/104; B01D 2255/106; B01D 2255/2065; B01D 2255/50; B01D 2255/1021; B01D 2255/20738; B01D 2255/20715; B01D 2255/1028; B01D 2255/9205; B01D 2255/2063; B01D 2255/9207; B01D 2255/2066; B01D 2255/9202; B01D 2255/20707; Y02P 20/52; Y02P 30/42; B01J 29/70; B01J 29/72; B01J 29/76; B01J 35/002; B01J 35/023; B01J 37/04; B01J 20/18; B01J 20/28002; B01J 20/28011; B01J 20/28004; B01J 35/1019; B01J 37/0045; B01J 37/009; B01J 37/06; C07C 11/04; C07C 11/06; C07C 11/08; C07C 1/20; C07C 2529/70; C01B 39/04; C01B 39/48
USPC .......... 502/60, 400, 407, 411, 414; 423/700, 423/701, 702, 703, 704, 710
See application file for complete search history.

(56) References Cited

U.S. PATENT DOCUMENTS 4,910,006 A 3/1990 Zones
4,963,337 A 10/1990 Zones
(Continued)

FOREIGN PATENT DOCUMENTS

EP 0 448 000 A1 9/1991
JP 5-502009 A 4/1993
(Continued)

OTHER PUBLICATIONS

International Search Report dated Jan. 10, 2017 in PCT/JP2016/085058, 2 pages.
(Continued)

*Primary Examiner* — Elizabeth D Wood
(74) *Attorney, Agent, or Firm* — Oblon, McClelland, Maier & Neustadt, L.L.P.

(57) ABSTRACT

A CON zeolite satisfying the following (1) to (2): (1) The framework is CON as per the code specified by the International Zeolite Association (IZA); and (2) It contains silicon and aluminum, and the molar ratio of aluminum to silicon is 0.04 or more.

11 Claims, 10 Drawing Sheets

Related U.S. Application Data of application No. 15/988,744, filed on May 24, 2018, now Pat. No. 10,478,810, which is a continuation of application No. PCT/JP2016/085058, filed on Nov. 25, 2016.

(51) Int. Cl.

| | | |
|---|---|---|
| *C07C 1/20* | (2006.01) | |
| *B01J 35/00* | (2006.01) | |
| *B01J 29/76* | (2006.01) | |
| *B01J 29/72* | (2006.01) | |
| *B01D 53/94* | (2006.01) | |
| *B01J 29/48* | (2006.01) | |
| *B01J 37/04* | (2006.01) | |
| *B01J 20/18* | (2006.01) | |
| *B01J 20/28* | (2006.01) | |
| *C01B 39/48* | (2006.01) | |
| *B01J 35/02* | (2006.01) | |
| *C01B 39/04* | (2006.01) | |

(52) U.S. Cl.
CPC .............. *Y02P 20/52* (2015.11); *Y02P 30/20* (2015.11); *Y02P 30/40* (2015.11)

(56) References Cited

U.S. PATENT DOCUMENTS

| | | | |
|---|---|---|---|
| 5,512,267 | A | 4/1996 | Davis |
| 8,007,763 | B2 | 8/2011 | Zones |
| 8,778,171 | B2 | 7/2014 | Oliveri |
| 2003/0133870 | A1 | 7/2003 | Chen et al. |
| 2008/0159936 | A1 | 7/2008 | Zones |
| 2009/0060835 | A1 | 3/2009 | Burton, Jr. |
| 2009/0188834 | A1 | 7/2009 | Euzen et al. |
| 2013/0129611 | A1 | 5/2013 | Maurer et al. |
| 2013/0323164 | A1 | 12/2013 | Feyen et al. |
| 2014/0072494 | A1 | 3/2014 | Zones |
| 2016/0102590 | A1 | 4/2016 | Weiss |
| 2017/0369390 | A1 | 12/2017 | Ghashghaee |
| 2019/0284113 | A1 | 9/2019 | Abudawoud |
| 2019/0299197 | A1 | 10/2019 | Zuidema |

FOREIGN PATENT DOCUMENTS

| | | |
|---|---|---|
| JP | 2004-509044 A | 3/2004 |
| JP | 2010-506812 A | 3/2010 |
| JP | 2012-505146 A | 3/2012 |
| JP | 2013-245163 A | 12/2013 |
| WO | WO 02/070407 A1 | 9/2002 |
| WO | WO 2005/039761 A2 | 5/2005 |
| WO | WO 2006/032782 A1 | 3/2006 |
| WO | WO 2012/172765 A2 | 12/2012 |
| WO | WO 2013/028958 A1 | 2/2013 |

OTHER PUBLICATIONS

International Preliminary Report on Patentability and Written Opinion dated Jun. 7, 2018 in PCT/JP2016/085058 (submitting English translation only), 8 pages.

Yoshioka, M., et al., "Development of the CON-type Aluminosilicate Zeolite and its Catalytic Application for the MTO Reaction", ACS Catalysis, vol. 5, Jun. 4, 2015, pp. 4268-4275.

Lobo, R.F., et al., "CIT-1: A New Molecular Sieve with Intersecting Pores Bounded by 10- and 12-Rings", J. Am. Chem. Soc., vol. 117 No. 13, 1995, pp. 3766-3779.

Yoshioka, M., et al., "MTO reaction activity over CON-type Zeolites synthesized under different conditions", CSJ: The Chemical Society of Japan Koen Yokoshu, vol. 93 No. 2, 2013, 1G4-48, p. 458 with cover page (with English abstract).

Watanabe, Y., "Synthesis of CIT-1 and its application to HC trap", CSJ: The Chemical Society of Japan Koen Yokoshu, vol. 86 No. 1, 2006, 2D1-05, p. 126 (with English translation).

Combined Chinese Office Action and Search Report dated Apr. 10, 2020 in Chinese Patent Application No. 201680069104.5 (with unedited computer generated English translation), 13 pages.

Office Action as received in the corresponding Japanese patent application No. 2017-552744 dated Dec. 8, 2020 w/English translation, 8 pages.

Japanese Office Action dated Nov. 22, 2022 in Japanese Patent Application No. 2021-171670 (with unedited computer generated English Translation), 6 pages.

Office Action and Search Report dated Apr. 1, 2023, issued in corresponding Chinese Application No. 202110320447.7 (with machine English language translation).

ZEOLITE CATALYST AND METHOD FOR PRODUCING LOWER OLEFIN

CROSS-REFERENCE TO RELATED APPLICATION

This is a continuation of U.S. application Ser. No. 16/595,539 filed Oct. 8, 2019, which is a continuation of U.S. application Ser. No. 15/988,744 filed May 24, 2018, now U.S. Pat. No. 10,478,810, which is a continuation of International Application PCT/JP2016/085058, filed on Nov. 25, 2016, which designated the U.S., and claims priority from Japanese Patent Application 2015-229994 which was filed on Nov. 25, 2015, the entire contents of which are incorporated herein by reference.

TECHNICAL FIELD

The present invention relates to a zeolite catalyst and a method of producing a lower olefin using the same.

BACKGROUND ART

As a method of producing a lower olefin such as ethylene, propylene, and butene, steam cracking of naphtha, and fluid catalytic cracking of vacuum gas oil have been heretofore generally carried out. In recent years a metathesis reaction using ethylene and 2-butene as raw materials, and a MTO (methanol to olefin) process using methanol and/or dimethyl ether as a raw material have been known.

Meanwhile, ethylene production by ethane cracking using ethane contained in natural gas as a raw material has been rapidly expanding due to recent price decline of natural gas. However, since ethane cracking scarcely yields hydrocarbons having a carbon number of 3 or more, such as propylene, butadiene, and butene, unlike steam cracking of naphtha, the shortage of hydrocarbons having a carbon number 3 or more, especially propylene and butadiene, has been surfacing.

Therefore, as a production method by which olefins having a carbon number of 3 or more, such as propylene, may be produced selectively, and the production amount of ethylene is suppressed, a MTO process using methanol and/or dimethyl ether synthesized from inexpensive coal or natural gas as a raw material has been attracting attention.

For example, as disclosed in Patent Document 1 and Non-Patent Literature 1, by using a catalyst containing a zeolite having a CON framework (Zeolite CIT-1) as an active ingredient, propylene and butene may be produced in high yield from methanol and/or dimethyl ether as a raw material, and further by-production of ethylene during propylene production may be suppressed. However, for industrial implementation, a catalyst having even higher performance is required currently.

PRIOR ART DOCUMENT

Patent Document

Patent Document 1: JP-A-2013-245163

Non-Patent Literature

Non-Patent Literature 1: Am. Chem. Soc. Catal., 5, 4268-4275 (2015)

SUMMARY OF THE INVENTION

Problem to be Solved by Invention

By using the CON zeolite catalyst disclosed in Patent Document 1 or Non-Patent Literature 1, propylene and butene may be produced efficiently from methanol and dimethyl ether. In this regard, a CON zeolite catalyst has a structure in which 12-membered ring structures and 10-membered ring structures intersect in a zigzag manner, such that pores in three directions do not cross each other at one place. Therefore, the intersection space is small, and therefore it is conceivable that coke is scarcely generate by a reaction, and the reaction activity is not remarkably deteriorated to prolong advantageously the catalyst life. However, in Patent Document 1 and Non-Patent Literature 1, sufficient investigation has not been made with respect to the catalyst life of the CON zeolite catalyst, and there is still room for improvement in terms of the catalyst life. In other words, it is preferable to use a zeolite catalyst capable of maintaining a high conversion of raw materials over a long period of time.

An object of the present invention is therefore to provide a zeolite catalyst capable of maintaining a high conversion of raw materials over a long period of time, and a method of producing a lower olefin stably over a long period of time using the zeolite catalyst.

Means for Solving the Problem

Regarding prolongation of the life of a CON zeolite catalyst containing aluminum (Al) as a constituent element, the present inventors have obtained the following knowledge.

Regarding prolongation of the life of a CON zeolite catalyst containing aluminum (Al) as a constituent element, the present inventors have obtained the following knowledge.

(1) A catalyst, in which the ratio $((A_2/A_1) \times 100(\%))$ of the integrated intensity area $(A_2)$ of the signal intensity in a range from 57.5 ppm to 70 ppm to the integrated intensity area $(A_1)$ of signal intensity in a range from 45 ppm to 70 ppm is not less than 49.0% when analyzed by $^{27}$Al-MAS-NMR, has a longer catalyst life than a catalyst with the ratio less than 49.0%.

(2) When the primary particle diameter of the catalyst is smaller, the catalyst life may be further improved.

The present invention has been made based on the above findings.

That is, the first aspect of the present invention relates to a CON zeolite catalyst comprising aluminum (Al) as a constituent element, wherein the CON zeolite catalyst has a ratio $((A_2/A_1) \times 100(\%))$ of an integrated intensity area $(A_2)$ of signal intensity in a range from 57.5 ppm to 70 ppm to an integrated intensity area $(A_1)$ of signal intensity in a range from 45 ppm to 70 ppm is not less than 49.0% when analyzed by $^{27}$Al-MAS-NMR.

"A zeolite catalyst comprising aluminum (Al) as a constituent element" means a zeolite in which part of silicon in a silica network is substituted with aluminum.

"CON zeolite" means a zeolite having a CON type framework according to a code specified by the International Zeolite Association (IZA).

"Zeolite catalyst" means a zeolite in which part of silicon in the silica network is substituted with another element thereby the substituted part constitutes an acid site which has a catalytic function. With respect to the zeolite catalyst of the present invention, there is no particular restriction on a reaction where the catalytic function, it is preferable as a catalyst for a reaction to produce a lower olefin. It is also preferable as a catalyst for a reaction to produce a lower olefin from organic compounds having carbon number of 1 to 10, such as an olefin, an alcohol, and a paraffin, as a raw materials, more preferable as a catalyst for a reaction to produce ethylene, butene, hexane, ethanol, methanol, and dimethyl ether from the same raw materials, and further preferable as a catalyst for a reaction to produce methanol and/or dimethyl ether from the same raw materials.

"Signal intensity" and "integrated intensity area" are obtained when a zeolite catalyst is analyzed by $^{21}$Al-MAS-NMR under the following conditions. That is, after a zeolite catalyst is sampled and placed into a solid-state NMR sample tube, the zeolite catalyst is left to stand overnight or longer in a desiccator containing a saturated aqueous solution of ammonium chloride to sufficiently absorb moisture, then after tight closure of the sample tube, subjected to an analysis with Varian NMR Systems 400 WB, using a Single Pulse measurement method with a pulse width of 1 μs (equivalent to 22.5° pulse), a MAS rotation frequency of 12 kHz, a waiting time of 0.1 s a spectral width of 250 kHz, a measurement temperature of room temperature, and a cumulative number of 36000 times to obtain a NMR spectrum based on a reference material of a 1.0 M aluminum chloride aqueous solution (−0.10 ppm), and the signal intensity and integrated intensity area are calculated.

In the first aspect of the present invention, it is preferable that the average primary particle diameter is 1000 nm or less.

Both "primary particle diameter" and "average primary particle diameter" may be determined with a scanning electron microscope (SEM).

A "primary particle" refers to a smallest particle in which a grain boundary is not recognizable. When an SEM image of a zeolite catalyst is taken, the smallest particle, which belongs to a portion of zeolite in the SEM image, and in which a grain boundary is not recognized, is herein regarded as a "primary particle". In this regard, it is not necessary for primary particles to be present as independent particles, and they may form a secondary particle by aggregation or otherwise. Even if a secondary particle is formed, it is possible to distinguish primary particles on the surface of a secondary particle in the SEM image.

An "average primary particle diameter" is measured as follows. Namely, 50 primary particles included in an SEM image of a zeolite catalyst are randomly selected, the major axis length (the length of the longest line segment joining one edge and another edge of the primary particle) is measured for each of the selected 50 primary particles, and the arithmetic mean of the measured 50 major axis lengths is defined as the "average primary particle diameter". However, when the entire zeolite catalyst includes less than 50 primary particles, the respective major axis lengths of all the primary particles included in the zeolite catalyst are measured, and the mean value of them is deemed as the "average primary particle diameter".

In the first aspect of the present invention, the molar ratio (Si/Al) of silicon (Si) to aluminum (Al) is preferably 10 or more.

In the first aspect of the present invention, a zeolite catalyst is preferably a catalyst used for a reaction to form a lower olefin.

A second aspect of the present invention is a method of producing a lower olefin including a step of making a raw material containing methanol and/or dimethyl ether come into contact with the zeolite catalyst.

"Lower olefin" means ethylene, propylene, and butene. It is preferable that the portion of propylene and butene is higher.

Effect of the Invention

According to the present invention, there may be provided a zeolite catalyst capable of maintaining a high conversion of raw materials over a long period of time, and a method of producing a lower olefin stably over a long period of time by using the zeolite catalyst.

DESCRIPTION OF EMBODIMENTS

1. Zeolite Catalyst

A zeolite catalyst according to the present embodiment is a CON zeolite catalyst containing aluminum (Al) as a constituent element, wherein the CON zeolite catalyst has the ratio (($A_2/A_1$)×100(%)) of the integrated intensity area ($A_2$) of signal intensity in a range from 57.5 ppm to 70 ppm to the integrated intensity area ($A_1$) of signal intensity in a range from 45 ppm to 70 ppm is not less than 49.0% when analyzed by $^{27}$Al-MAS-NMR.

1.1. Composition 1.1.1. Aluminum (Al)

A zeolite catalyst according to the present embodiment contains aluminum (Al) as a constituent element. Namely, it has a constitution, where in a silica network of zeolite, part of silicon is substituted with aluminum, and a site substituted by aluminum constitutes an acid site and functions as a catalyst. In this regard, in a zeolite catalyst according to the present invention, the site of aluminum in the zeolite framework may be different from the conventional one.

Figure 1:
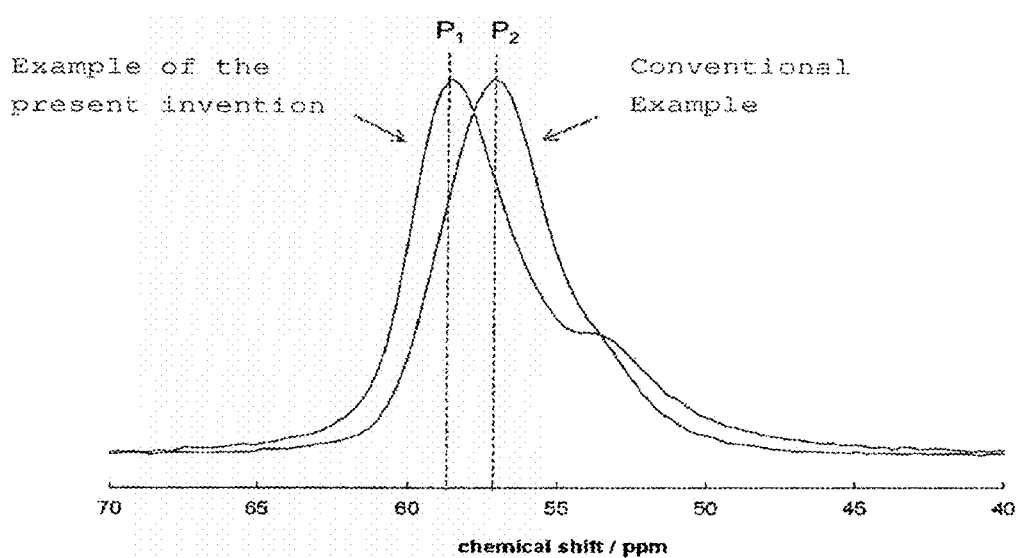
FIG. 1 is a chart showing an example of a $^{27}$Al-MAS-NMR spectrum of a CON zeolite catalyst (aluminosilicate) according to the present embodiment, and an example of a $^{27}$Al-MAS-NMR spectrum of a conventional CON zeolite catalyst (aluminosilicate).

FIG. 1 shows an example of a $^{27}$Al-MAS-NMR spectrum of a zeolite catalyst according to the present embodiment, and an example of a $^{27}$Al-MAS-NMR spectrum of a conventional zeolite catalyst. As shown in FIG. 1, in the zeolite catalyst according to present embodiment, the peak top of the peak present in a range from 50 ppm to 65 ppm is shifted from the position $P_2$ to the position $P_1$ as compared with a conventional zeolite catalyst.

As described above, a zeolite catalyst according to the present embodiment exhibits a shifted position of the peak attributable to aluminum in the zeolite framework to give the above-mentioned $A_2/A_1$ value different from that of a conventional zeolite catalyst. That is, a zeolite catalyst according to the present embodiment is in part characterized in that the ratio of the integrated intensity areas (($A_2/A_1$)×100(%)) is 49.0% or more. The ratio is preferably 49.5% or more, more preferably 50.0% or more, and especially preferably 51.0% or more. Although there is no particular restriction on the upper limit of the ratio, it is usually 100.0% or less, preferably 90.0% or less, and more preferably 80.0, or less.

In a zeolite catalyst according to the present embodiment, the molar ratio (Si/Al) of silicon (Si) to aluminum (Al) is preferably 10 or more, more preferably 20 or more, further preferably 50 or more, and especially preferably 100 or more. It is preferably 1500 or less, more preferably 1000 or less, and especially preferably 750 or less. By limiting the Si/Al within such a range, it is possible to obtain a zeolite catalyst having sufficient catalytic activity, and at the same time having an improved catalyst life.

1.1.2. Elements Other than Al

A zeolite catalyst according to the present embodiment may further include one or more constituent elements selected from boron (B), zinc (Zn), and germanium (Ge). By including the elements, a CON zeolite may be easily synthesized. As described later, a zeolite catalyst according to the present embodiment may be produced easily by removing part of boron and zinc from the framework of borosilicate, borozincosilicate, zincosilicate, or the like, and introducing aluminum into the site. Also, from this viewpoint, boron, etc. may remain in the zeolite catalyst.

Although there is no particular restriction on the molar ratio (Si/B) of silicon (Si) to boron (B) in a zeolite catalyst according to the present embodiment, it is preferably 50 or more, more preferably 100 or more, and especially preferably 200 or more. Although there is also no particular restriction on the molar ratio (Si/Zn) of silicon (Si) to zinc (Zn), it is preferably 50 or more, more preferably 100 or more, and especially preferably 200 or more. Although there is also no particular restriction on the molar ratio (Si/Ge) of silicon (Si) to germanium (Ge), it is preferably 50 or more, more preferably 100 or more, and especially preferably 200 or more. In addition, there is no particular restriction on the molar ratio (Si/(B+Zn)) of silicon (Si) to the total of the above B element and Zn element (B+Zn), it is preferably 50 or more, more preferably 100 or more, and especially preferably 200 or more. Furthermore, there is no particular restriction on the molar ratio (Si/(B+Zn+Ge)) of silicon (Si) to the total of the above B element, Zn element, and Ge element (B+Zn+Ge), it is preferably 50 or more, more preferably 100 or more, and especially preferably 200 or more. The upper limits of the molar ratios (Si/B), (Si/Zn), (Si/Ge), (Si/(B+Zn)), and (Si/(B+Zn+Ge)) may be, for example, 100000 or less, 50000 or less, or 10000 or less. By adjusting the molar ratio of silicon to the element(s) within such a range, it becomes possible to introduce aluminum easily to vacant sites after removing part of boron or zinc from the framework.

Further, a zeolite catalyst according to the present embodiment may include gallium (Ga), iron (Fe), and the like, in addition to aluminum, as a constituent element which substitutes silicon and functions as an acid site.

1.2. Crystal Structure

It is important that a zeolite catalyst according to the present embodiment has a CON type framework as per the code specified by the International Zeolite Association (IZA). A CON zeolite catalyst has as a constitutional unit, a 3-dimensional pore structure in which two 12-membered ring structures and one 10-membered ring structure cross each other. The CON zeolite catalyst having the 12-membered ring structures is more advantageous to pore diffusion of a reaction product than a CHA zeolite constituted solely with 8-membered ring structures, or an MFI zeolite constituted solely with 10-membered ring structures, so as to form a catalyst superior in selectivity for an olefin with a carbon number of 3 or more. Meanwhile, a CON zeolite catalyst has an advantage that the catalyst life is long, conceivably because the pores in three directions do not intersect at one place, and an intersection space is small, so that coke is less likely to be formed by a reaction and remarkable deterioration of the reaction activity is less likely to be incurred. In addition to the above feature, the site of aluminum in the crystal structure according to the present embodiment may be different from a conventional site, and the catalyst life may be further improved.

Whether a zeolite catalyst has a CON framework or not may be judged by performing an X-ray diffraction analysis using CuKα as a radiation source and matching the obtained profile with the profiles registered in the X-ray diffraction intensity database (PDF #00-050-1694). According to the database, a diffraction peak attributed to the (130) plane is to be recognized in the vicinity of 2θ=20.4°, and a diffraction peak attributed to the (510) plane is to be recognized in the vicinity of 2θ=22.1°.

As described below, the size of a primary particle in a zeolite catalyst according to the present embodiment is small. The size of a primary particle in a zeolite catalyst affects the half width of a diffraction peak in a powder X-ray diffraction analysis. In other words, the smaller the primary particle becomes, the larger the half width tends to become.

From this point of view, in a zeolite catalyst according to the present embodiment, the half width of the peak attributable to the (130) plane obtained by a powder X-ray diffraction analysis (Radiation source: CuKα, reading width: any width from 0.0150 to 0.020°, and scanning speed: any speed from 2.0°/min to 20.0°/min) is preferably from 0.100 to 0.25°. It is more preferably 0.120 or more, further preferably 0.14° or more, and especially preferably 0.160 or more. Further, it is more preferably 0.220 or less, and especially preferably 0.200 or less.

In addition, in a zeolite catalyst according to the present embodiment, the half width of the peak attributable to the (510) plane obtained by a powder X-ray diffraction analysis (Radiation source: CuKα, reading width: any width in a range from 0.0150 to 0.0200, and scanning speed: any speed in a range from 2.0°/min to 20.0°/min) is preferably from 0.10° to 0.25°. It is more preferably 0.120 or more, further preferably 0.140 or more, and especially preferably 0.16° or more. Further, it is more preferably 0.220 or less, and especially preferably 0.200 or less.

When it is 0.10° or more, the primary particle tends to be small, which is preferable. When it is 0.25° or less, the primary particle is large enough not to contain an amorphous part, which is also preferable. In this regard, the "half width of the peak of the (130) plane", and "the half width of the peak of the (510) plane" in the present embodiment are values obtained by the following method. Namely, firstly from the obtained diffraction profile, a diffraction peak near 2θ=20.4° attributable to the (130) plane and a diffraction peak near 2θ=22.1° attributable to the (510) plane are detected. Then, the peak is cut out in the range of 19° to 26°, and after performing subtraction of the background and making Kα1 and Kα2 separation, the half width of Kα1 is read. For this analysis, an analysis software "JADE" is used. In this regard, the half width means the width of 2θ at an intensity half the maximum intensity of the peak.

1.3. Shape

There is no particular restriction on the shape of a zeolite catalyst according to the present embodiment, and it may be particulate (powdery) or massive form, or may be formed to various shapes using a material inert to the reaction or a binder. Examples of the material inert to the reaction or the binder include alumina or alumina sol, silica, silica gel, a silicate, quartz, and mixtures thereof. Among them, alumina is preferable from the viewpoint that a firm formed article may be formed as an industrial catalyst. Addition of these materials is effective in reducing the cost of a whole catalyst and acting as a heat sink for assisting thermal shield during regeneration of the catalyst, and also effective in increasing the density of the catalyst, and increasing the catalyst strength.

In particular, it is preferable that a zeolite catalyst according to the present embodiment is composed of small primary particles. When the primary particle is reduced in size by suppressing the crystal growth as above, the catalyst life may be further improved.

Specifically, a zeolite catalyst according to the present embodiment preferably has an average primary particle diameter of 1000 nm or less, more preferably 700 nm or less, further preferably 300 nm or less, and especially preferably 200 nm or less. Although there is no particular restriction on the lower limit of the average primary particle diameter, it is usually 20 nm or more, preferably 40 nm or more, and especially preferably 60 nm or more. The definition of a primary particle diameter and the calculation method of an average primary particle diameter are as described above. When the primary particle is small, the primary particles are likely to agglomerate and form secondary particles. However, even if secondary particles are formed, it is possible to distinguish each primary particle existing on the surface of a secondary particle in an SEM image, and the average primary particle diameter may be calculated.

There is no particular restriction on the BET specific surface area of a zeolite catalyst according to the present embodiment, and it is usually 200 $m^2/g$ or more, preferably 250 $m^2/g$ or more, and more preferably 300 $m^2/g$ or more; and is usually 1000 $m^2/g$ or less, preferably 800 $m^2/g$ or less, and more preferably 700 $m^2/g$ or less.

There is no particular restriction on the pore volume of a zeolite catalyst according to the present embodiment, and it is usually 0.1 mL/g or more, and preferably 0.2 mL/g or more; and is usually 3 mL/g or less, and preferably 2 mL/g or less.

1.4. Others

There is no particular restriction on the ion exchange site of a zeolite catalyst according to the present embodiment, and it may be an H type or a site exchanged with a metal ion. Examples of the metal ion include an alkali metal ion and an alkaline earth metal ion.

As described above, in a zeolite catalyst according to the present invention, the site of aluminum in the zeolite framework may be different from the conventional site, and the above ratio (($A_2/A_1$)×100(%)) is 49.0% or more. As a result, the catalyst life is improved as compared with a catalyst having the ratio of less than 49.0%. In addition, when the primary particle diameter of the zeolite catalyst is small (or when the half width of the X-ray diffraction peak is large), the catalyst life is further improved.

2. Method of Producing Zeolite Catalyst

A zeolite catalyst according to the present embodiment may be produced easily by a method in which, for example, a CON type crystalline borosilicate containing at least boron (B) as a constituent element is synthesized, then B in the framework is removed, and Al is introduced in at least part of vacant sites (post-treatment method).

2.1. Synthesis of Crystalline Borosilicate

The crystalline borosilicate may be synthesized by a hydrothermal synthesis method. For example, an alkali metal source, a boron source, and a structure-directing agent (preferably N,N,N-trimethyl-(−)-cis-myrtanylammonium hydroxide) are added to water and stirred, then a silica source is added thereto to form a uniform gel, and the obtained raw material gel is kept in a pressurized heating vessel at 120 to 200° C. to be crystallized. In this connection, from the viewpoint of producibility, it is preferable to add a seed crystal at the time of crystallization. Next, after filtration and washing of the crystallized raw material gel, the solid content is dried at 100 to 200° C., and subsequently calcined at 400 to 900° C. to obtain powdery crystalline borosilicate.

In this regard, as an alkali metal source, one or more selected from hydroxides, chlorides, bromides, iodides, hydrogencarbonates, carbonates, and the like of lithium, sodium, potassium, rubidium, and cesium may be used. As a boron source, one or more selected from boric acid, sodium borate, boron oxide, and the like may be used. As a silica source, one or more selected from a silicate, such as fumed silica, silica sol, silica gel, silicon dioxide, and water glass, an alkoxide of silicon, such as tetraethoxyorthosilicate and tetramethoxysilane, a halide of silicon, and the like may be used.

Incidentally, the crystalline borosilicate may contain zinc (Zn), aluminum (Al), gallium (Ga), iron (Fe), etc. as a constituent element in addition to boron (B). Namely, a crystalline borozincosilicate, a crystalline boroaluminosilicate, a crystalline borogallosilicate, a crystalline boroferrisilicate, or the like may be used instead of a crystalline borosilicate. In this case, in addition to the boron source or the silica source, a zinc source, an aluminum source, a gallium source, and an iron source may be added in forming the gel.

In this case, as the zinc source, one or more selected from zinc acetate, zinc sulfate, zinc nitrate, zinc hydroxide, and the like may be used. As the aluminum source, one or more selected from aluminum sulfate, aluminum nitrate, pseudo-boehmite, an aluminum alkoxide, aluminum hydroxide, alumina sol, sodium aluminate, and the like may be used. As the gallium source, one or more selected from gallium nitrate, gallium sulfate, gallium phosphate, gallium chloride, gallium bromide, gallium hydroxide, and the like may be used. As the iron source, one or more selected from iron nitrate, iron sulfate, iron oxide, iron chloride, iron hydroxide, and the like may be used.

As a seed crystal, a BEA-type, a CON-type, an MSE-type zeolite, and the like may be used. As the seed crystal, either a zeolite which contains a structure-directing agent, but is not calcined after hydrothermal synthesis, or a zeolite which is calcined but does not contain a structure-directing agent, may be used. There is no particular restriction on the composition of a zeolite to be used as a seed crystal, insofar as it does not greatly affect the composition of the mixture. Although there is no particular restriction on the particle diameter of a zeolite to be used as a seed crystal, it is preferably from 20 nm to 2000 nm in terms of an average primary particle diameter. It is preferably 40 nm or more, and more preferably 1000 nm or less. When the average primary particle diameter of a seed crystal is adjusted within the above range, dissolution of a seed crystal in the mixture proceeds sufficiently, and crystallization of a CON zeolite may be promoted.

In the synthesis of the crystalline borosilicate (crystalline borozincosilicate, crystalline boroaluminosilicate, crystalline borogallosilicate, and crystalline boroferrisilicate), the molar ratio (Si/B) of silicon (Si) to boron (B) is preferably 50 or less, more preferably 30 or less, further preferably 20 or less, and especially preferably 10 or less. It has been found that by charging raw materials at a low Si/B ratio, the primary particle of a CON zeolite becomes smaller and the catalyst life is improved. Although there is no particular restriction on the lower limit of the molar ratio (Si/B), it is preferably 3 or more, and more preferably 5 or more.

Although there is no particular restriction on the molar ratio (Si/Zn) of silicon (Si) to zinc (Zn) in the raw material mixture in synthesizing a crystalline borozincosilicate, it is preferably from 50 to 400. The lower limit is more preferably 75 or more, and especially preferably 100 or more, and the upper limit is more preferably 250 or less, and especially preferably 150 or less.

Although there is no particular restriction on the molar ratio (Si/Ge) of silicon (Si) to germanium (Ge) in the raw material mixture in synthesizing a crystalline borogermanosilicate, it is preferably from 5 to 100. The lower limit is more preferably 7 or more, and especially preferably 10 or more; and the upper limit is more preferably 75 or less, and especially preferably 50 or less.

The molar ratio (M/Si) of an alkali metal element (M) to silicon (Si) in the raw material mixture is preferably from 0 to 0.3. The lower limit is more preferably 0.05 or more, and especially preferably 0.08 or more, and the upper limit is more preferably 0.20 or less, and especially preferably 0.12 or less. By adjusting the M/Si within the above range, crystallization of a CON zeolite is promoted and the zeolite may be synthesized in high yield.

The molar ratio (SDA/Si) of a structure-directing agent (SDA) to silicon (Si) in the raw material mixture is preferably from 0 to 0.5, more preferably 0.10 or more, and especially preferably 0.20 or more; and more preferably 0.40 or less, and especially preferably 0.30 or less. By adjusting the SDA/Si within the above range, crystallization of a CON zeolite is promoted, and the zeolite may be synthesized in high yield. In addition, the cost of the raw material (structure-directing agent) may be suppressed.

Although there is no particular restriction on the proportion of water in the raw material mixture, the molar ratio ($H_2O$/Si) of water ($H_2O$) to silicon (Si) is preferably from 10 to 100. It is more preferably 15 or more, and especially preferably 20 or more; and is more preferably 60 or less, and especially preferably 30 or less. When the proportion of water in the mixture is within the above range, it is possible to suppress deterioration of mixability in stirring due to viscosity increase during a reaction. Further, the productivity per reactor may be increased.

Although there is no particular restriction on the proportion of a seed crystal in the raw material mixture, the molar ratio (Seed/Si) of a seed crystal (Seed) to silicon (Si) is preferably from 0 to 0.10, more preferably 0.01 or more, and especially preferably 0.02 or more; and is more preferably 0.05 or less, and especially preferably 0.03 or less. When the amount of the seed crystal is within the above range, the amount of a precursor directed to the CON framework becomes sufficient, and crystallization may be promoted. In addition, since the content of a component derived from the seed crystal in the product is suppressed and the productivity may be enhanced, so that the production cost may be reduced.

Although there is no particular restriction on the hydrothermal synthesis temperature, it is preferably from 120° C. to 200° C., more preferably 150° C. or higher, and especially preferably 160° C. or higher; and is more preferably 190° C. or lower, and especially preferably 180° C. or lower. By adjusting the reaction temperature within the above range, the crystallization time of a CON zeolite may be shortened. Further, a zeolite with small sized primary particles may be synthesized.

Although there is no particular restriction on the hydrothermal synthesis time, it is preferably from 12 hours to 20 days. The lower limit is more preferably 1 day or more, and especially preferably 3 days or more; and the upper limit is more preferably 14 days or less, and especially preferably 9 days or less.

2.2. Removal of B and Introduction of Al

There is no particular restriction on a method of removing B from the framework of a crystalline borosilicate, and a conventionally known method, such as acid a treatment and a steam treatment, may be adopted. The same is true for a method of removing B and Zn from a crystalline borozincosilicate, a method of removing B from a crystalline borogallosilicate, a method of removing B from a crystalline boroaluminosilicate, and a method of removing B from a crystalline boroferrisilicate.

There is no particular restriction on a method of introducing Al to a crystalline borosilicate, from which B has been removed, into at least part of the sites deprived of B. For example, there is a method in which a crystalline borosilicate after removal of B is added together with an aluminum source to water, which is stirred and then heated. In this case, as an aluminum source, any one appropriately selected from the above may be used.

The molar ratio (Si/Al) of silicon (Si) to aluminum (Al) during a post-treatment is preferably from 10 to 1500. The lower limit is more preferably 50 or more, and especially preferably 100 or more; and the upper limit is more preferably 1000 or less, and especially preferably 750 or less. By adjusting the Si/Al within the range, it is possible to obtain a zeolite catalyst having sufficient catalytic activity and having a further improved catalyst life.

Although there is no particular restriction on the heating temperature, it is preferably from 60° C. to 200° C. The lower limit is more preferably 80° C. or higher, and especially preferably 100° C. or higher; and the upper limit is more preferably 175° C. or lower, and especially preferably 150° C. or lower.

2.3. Other Post-Treatment Methods

In the above post-treatment method, a method of introducing Al after removing boron from a crystalline borosilicate has been described. In addition, it is possible to perform a post-treatment method, in which a silicate containing zinc (Zn), a silicate containing germanium (Ge), or the like is synthesized in advance, the zinc, germanium, or the like is removed, and then Al is introduced.

In this case, the synthesis of the silicate containing zinc (Zn), the silicate containing germanium (Ge), etc. may be carried out as in 2.1., and the removal of Zn, Ge, etc. and introduction of Al may be carried out as in 2.2.

Examples of an element which may be contained in a silicate include elements in the fourth period of the periodic table, elements in groups 12 to 15 in the periodic table, or elements satisfying both of them, which example is zinc or germanium. An exemplar molar ratio of the above elements in a zeolite catalyst according to the present embodiment is the same as the aforedescribed Si/Zn ratio and Si/(B+Zn) ratio. An exemplar molar ratio of the above elements in the raw material mixture is the same as the Si/Zn ratio in the synthesis of a crystalline borozincosilicate, or the Si/Ge ratio in the synthesis of a crystalline borogermanosilicate synthesis. Two or more of the above elements may be used in combination. It is conceivable that the above element occupies a specific site in the zeolite framework, and the element at such a specific site (for example, a site different from the conventional site) is replaced with aluminum to yield a zeolite according to the present embodiment.

On the other hand, when the molar ratio (Si/Al) of a zeolite catalyst is adjusted within a specific range (for example, the lower limit is set at a specific value), a zeolite catalyst according to the present embodiment may be also obtained. In this case, the molar ratio (Si/Al) of a zeolite catalyst according to the present embodiment may be higher than 100, higher than 130, higher than 170, higher than 200, higher than 230, or higher than 250, while an exemplar upper limit is as described above. When the zeolite catalyst is produced, the molar ratio (Si/Al) of silicon (Si) to aluminum (Al) during a post-treatment (representing herein the molar ratio of Si in a silicate to be subjected to a post-treatment to Al in an aluminum source to be used in the post-treatment method) may be higher than 150, higher than 200, higher than 250, higher than 300, and higher than 350. Meanwhile, an exemplar upper limit is as described above.

When a silicate contains the above element, such as zinc and germanium, or when the molar ratio (Si/Al) in a zeolite catalyst is increased, a zeolite catalyst according to the present embodiment tends to be obtained easily, even if the Si/B ratio in the raw material mixture for the silicate is not low (for example, when the Si/B ratio is higher than 10, or higher than 20).

A zeolite catalyst according to the present embodiment may be produced by a combination of 2 or more methods of the method in which raw materials are charged at a low Si/B ratio, the method including elements such as zinc and germanium, and the method in which the molar ratio (Si/Al) is adjusted at a high level.

Although the methods of producing a zeolite catalyst according to the present invention by a post-treatment method have been described above, a method of producing a zeolite catalyst according to the present embodiment is not limited to a post-treatment method.

3. Method of Producing Lower Olefin

Another aspect of the present invention is a method of producing a lower olefin by the MTO method. In other words, it is a method of producing a lower olefin involving a step of making a raw material containing methanol and/or dimethyl ether come into contact with a zeolite catalyst according to the present embodiment. Lower olefin refers to ethylene, propylene, and butene. Particularly, those containing large amounts of propylene and butene are preferable.

The lower olefin produced according to the present embodiment may contain, for example, propylene at a content of 30 to 70 mol %, butene at a content of 10 to 40 mol %, and ethylene at a content of 1 to 15 mol %.

Since details of methanol or dimethyl ether as a raw material, reaction procedures, and reaction conditions for the MTO method are publicly known, detailed explanation is omitted herein. For example, [methanol, and dimethyl ether], and [reaction procedures, and conditions] disclosed in Patent Document 1 (Japanese Unexamined Patent Application Publication No. 2013-245163) may be adopted.

Since a zeolite catalyst having an improved catalyst life is used in the production method of a lower olefin according to the present embodiment, it is possible to produce a lower olefin stably over a long period of time.

EXAMPLE

Hereinafter, the present invention will be described specifically below referring to examples, provided that the present invention be not limited in any way to the following examples.

1. Synthesis of CON Zeolite Catalyst (Aluminosilicate)

Example 1

Synthesis of Crystalline Borosilicate

Firstly, 0.81 g of a 1.0 M sodium hydroxide aqueous solution, 1.18 g of an aqueous solution of 1.05 M N,N,N-trimethyl-(-)-cis-myrtanylammonium hydroxide (hereinafter abbreviated as "TMMAOH"), and 1.99 g of water were mixed, thereto 0.0825 g of boric acid was added, and the mixture was stirred, to which 0.405 g of fumed silica (Cab-O-Sil M-7D, produced by Cabot Corporation) was added as a silica source, and further stirred sufficiently. Further, 0.0081 g of BEA type borosilicate was added as a seed crystal, and the mixture was stirred to prepare a reaction mixture (hereinafter occasionally referred to as "raw material gel").

The prepared raw material gel was charged into an autoclave and heated at 170° C. for 9 days with stirring at 40 rpm. The product was filtrated, washed with water, and then dried at 100° C. overnight. After drying, it was calcined in an air atmosphere at 600° C. for 6 hours to yield 0.397 g of a sodium type zeolite powder (borosilicate).

(Removal of B and Introduction of Al)

The following operation (post-treatment) was carried out for the purpose of removing boron in the zeolite framework of the obtained borosilicate and replacing it with aluminum. Into 20 mL of a 2 N nitric acid aqueous solution, 0.2 g of the obtained borosilicate was added, and the mixture was stirred at 100° C. at reflux for 20 hours. Thereafter, the zeolite was filtrated, washed with water, and then dried at 100° C. overnight to yield a protonic zeolite powder (silicate). The whole amount of the yielded powder was added to 20 g of an aqueous solution having dissolved 0.0031 g of aluminum nitrate nonahydrate, and the mixture was stirred at 100° C. at reflux for 2 days. Thereafter, the zeolite was filtrated, washed with water, and then dried at 100° C. overnight to obtain 0.154 g of a protonic zeolite powder (aluminosilicate).

Example 2

Synthesis of Crystalline Borozincosilicate

Firstly, 0.54 g of a 1.0 M sodium hydroxide aqueous solution, 0.79 g of a 1.05 M TMMAOH aqueous solution, and 1.43 g of water were mixed, thereto 0.0275 g of boric acid, and 0.0041 g of zinc acetate were added, and the mixture was stirred, to which 0.27 g of fumed silica (Cab-O-Sil M-7D, produced by Cabot Corporation) was added as a silica source, and further stirred sufficiently. Further, 0.0054 g of a BEA type borosilicate was added as a seed crystal, and the mixture stirred to prepare a raw material gel.

The prepared raw material gel was charged into an autoclave and heated at 170° C. for 7 days with stirring at 40 rpm. The product was filtrated, washed with water, and then dried at 100° C. overnight. After drying, it was calcined in an air atmosphere at 600° C. for 6 hours to yield 0.213 g of a sodium type zeolite powder (borozincosilicate).

(Removal of B and Zn, and Introduction of Al)

The post-treatment was carried out for the purpose of removing boron and zinc in the zeolite framework of the obtained borozincosilicate and replacing them with aluminum. The post-treatment was carried out in the same manner as in Example 1 to obtain 0.162 g of a protonic zeolite powder (aluminosilicate).

Example 3

Synthesis of Crystalline Borozincosilicate

Firstly, 0.45 g of a 1.0 M sodium hydroxide aqueous solution, 0.79 g of a 1.05 M TMMAOH aqueous solution, and 1.43 g of water were mixed, thereto 0.011 g of boric acid, and 0.0082 g of zinc acetate were added, and the mixture was stirred, to which 0.27 g of fumed silica (Cab-O-Sil M-7D, produced by Cabot Corporation) was added as a silica source, and further stirred sufficiently. Further, 0.0054 g of a BEA type borosilicate was added as a seed crystal and the mixture stirred to prepare a raw material gel.

The prepared raw material gel was charged into an autoclave and heated at 170° C. for 7 days with stirring at 40 rpm. The product was filtrated, washed with water, and then dried at 100° C. overnight. After drying, it was calcined in an air atmosphere at 600° C. for 6 hours to yield 0.228 g of a sodium type zeolite powder (borozincosilicate).

(Removal of B and Zn, and Introduction of Al)

The post-treatment was carried out for the purpose of removing boron and zinc in the zeolite framework of the obtained borozincosilicate and replacing them with aluminum. The post-treatment was carried out in the same manner as in Example 1 to obtain 0.151 g of a protonic zeolite powder (aluminosilicate).

Example 4

Synthesis of Crystalline Boroaluminosilicate

Firstly, 0.36 g of a 1.0 M sodium hydroxide aqueous solution, 0.79 g of a 1.05 M TMMAOH aqueous solution, and 0.72 g of water were mixed, thereto 0.011 g of boric acid, and 0.0109 g of aluminum sulfate were added, and the mixture was stirred, to which 0.27 g of fumed silica (Cab-O-Sil M-7D, produced by Cabot Corporation) was added as a silica source, and further stirred sufficiently. Further, 0.0054 g of a BEA type borosilicate was added as a seed crystal, and the mixture was stirred to prepare a raw material gel.

The prepared raw material gel was charged into an autoclave and heated at 200° C. for 2 days with stirring at 40 rpm. The product was filtrated, washed with water, and then dried at 100° C. overnight. After drying, it was calcined in an air atmosphere at 600° C. for 6 hours to yield 0.260 g of a sodium type zeolite powder (boroaluminosilicate).

(Removal of B and Introduction of Al)

The post-treatment was carried out for the purpose of removing boron in the zeolite framework of the obtained borosilicate and replacing it with aluminum. Into 25 mL of a 2 N nitric acid aqueous solution, 0.25 g of the obtained boroaluminosilicate was added, and the mixture was stirred at 100° C. at reflux for 20 hours. Thereafter, the zeolite was filtrated, washed with water, and then dried at 100° C. overnight to yield a protonic zeolite powder (aluminosilicate). The whole amount of the yielded powder was added to 20 g of an aqueous solution having dissolved 0.0010 g of aluminum nitrate nonahydrate, and the mixture was stirred at 100° C. at reflux for 2 days. Thereafter, the zeolite was filtrated, washed with water and then dried at 100° C. overnight to obtain 0.175 g of a protonic zeolite powder (aluminosilicate).

Comparative Example 1

Firstly, 0.54 g of a 1.0 M sodium hydroxide aqueous solution, 0.79 g of a 1.05 M TMMAOH aqueous solution, and 1.33 g of water were mixed, thereto 0.055 g of boric acid and 0.0030 g of aluminum sulfate were added, and the mixture was stirred, to which 0.27 g of fumed silica (Cab-O-Sil M-7D, produced by Cabot Corporation) was added as a silica source, and further stirred sufficiently. Further, 0.0054 g of a BEA type borosilicate was added as a seed crystal, and the mixture was stirred to prepare a raw material gel.

The prepared raw material gel was charged into an autoclave and heated at 170° C. for 10 days with stirring at 40 rpm. The product was filtrated, washed with water, and then dried at 100° C. overnight. After drying, it was calcined in an air atmosphere at 600° C. for 6 hours to yield 0.260 g of a sodium type zeolite powder (boroaluminosilicate).

The obtained powder was ion exchanged at 80° C. for 1 hour in a 2N aqueous solution of ammonium nitrate and then filtrated. The powder obtained by filtration was ion-exchanged again in a 2N aqueous solution of ammonium nitrate at 80° C. for 1 hour, then filtrated and dried to obtain an ammonium type zeolite. Thereafter, it was calcined in an air atmosphere at 600° C. to obtain a protonic zeolite (aluminosilicate).

Comparative Example 2

Synthesis of Crystalline Borosilicate

Firstly, 0.9 g of a 1.0 M sodium hydroxide aqueous solution, 1.58 g of a 1.05 M TMMAOH aqueous solution, and 7.72 g of water were mixed, thereto 0.022 g of boric acid was added, and the mixture was stirred, to which 0.54 g of fumed silica (Cab-O-Sil M-7D, produced by Cabot Corporation) was added as a silica source, and further stirred sufficiently. Further, 0.0108 g of a BEA type borosilicate was added as a seed crystal, and the mixture was stirred to prepare a raw material gel.

The prepared raw material gel was charged into an autoclave and heated at 150° C. for 21 days in a state of being left still. The product was filtrated, washed with water, and then dried at 100° C. overnight. After drying, it was calcined in an air atmosphere at 600° C. for 6 hours to yield 0.438 g of a sodium type zeolite powder (borosilicate).

(Removal of B and Introduction of Al)

The following post-treatment was carried out for the purpose of removing boron in the zeolite framework of the obtained borosilicate and replacing it with aluminum. Into 40 mL of a 0.01 M hydrochloric acid aqueous solution, 0.4 g of the obtained borosilicate was added, and the mixture was stirred at 100° C. at reflux for 24 hours. Thereafter, the zeolite was filtered, washed with water, and then dried at 100° C. overnight to yield a protonic zeolite powder (silicate). The whole amount of the yielded powder was added to 17.5 g of an aqueous solution having dissolved 0.70 g of aluminum nitrate nonahydrate, and the mixture was stirred at 100° C. at reflux for 12 hours. Thereafter, the zeolite was filtrated, washed with water and then dried at 100° C. overnight to obtain 0.328 g of a protonic zeolite powder (aluminosilicate).

Comparative Example 3

Firstly, 0.45 g of a 1.0 M sodium hydroxide aqueous solution, 0.79 g of a 1.05 M TMMAOH aqueous solution, and 1.43 g of water were mixed, thereto 0.011 g of boric acid and 0.0038 g of aluminum sulfate were added, and the mixture was stirred, to which 0.27 g of fumed silica (Cab-O-Sil M-7D, produced by Cabot Corporation) was added as a silica source, and further stirred sufficiently. Further, 0.0054 g of a BEA type borosilicate was added as a seed crystal, and the mixture was stirred to prepare a raw material gel.

The prepared raw material gel was charged into an autoclave and heated at 170° C. for 7 days in a state of being left still. The product was filtrated, washed with water, and then dried at 100° C. overnight. After drying, it was calcined in an air atmosphere at 600° C. for 6 hours to yield 0.213 g of a sodium type zeolite powder (boroaluminosilicate). A protonic zeolite (aluminosilicate) was obtained by conducting subsequent ion exchange and calcination in the same manner as in Example 5.

Comparative Example 4

A protonic zeolite (aluminosilicate) was yielded by conducting ion exchange and calcination in the same manner as in Comparative Example 1 on the sodium type zeolite powder (boroaluminosilicate) obtained after the hydrothermal synthesis in Example 4.

Comparative Example 5

The protonic zeolite powder (aluminosilicate) yielded after the nitric acid treatment, filtration and drying in Example 4 was directly used as a zeolite catalyst.

Example 5

Synthesis of Crystalline Borosilicate

Firstly, 0.45 g of a 1.0 M sodium hydroxide aqueous solution, 0.63 g of a 1.32 M TMMAOH aqueous solution, and 1.99 g of water were mixed, thereto 0.011 g of boric acid was added, and the mixture was stirred, to which 0.27 g of fumed silica (Cab-O-Sil M-7D, produced by Cabot Corporation) was added as a silica source, and further stirred sufficiently. Further, 0.0054 g of a BEA type borosilicate was added as a seed crystal, and the mixture was stirred to prepare a raw material gel.

The prepared raw material gel was charged into an autoclave and heated at 170° C. for 4 days with stirring at 40 rpm. The product was filtrated, washed with water, and then dried at 100° C. overnight. After drying, it was calcined in an air atmosphere at 600° C. for 6 hours to yield 0.214 g of a sodium type zeolite powder (borosilicate).

(Removal of B and Introduction of Al)

The post-treatment was carried out for the purpose of removing boron in the zeolite framework of the obtained borosilicate and replacing them with aluminum. The post-treatment was carried out in the same manner as in Example 1 to obtain 0.155 g of a protonic zeolite powder (aluminosilicate).

Example 6

Synthesis of Crystalline Borogermanosilicate

Firstly, 0.45 g of a 1.0 M sodium hydroxide aqueous solution, 0.63 g of a 1.32 M TMMAOH aqueous solution, and 1.99 g of water were mixed, thereto 0.011 g of boric acid, and 0.028 g of germanium oxide were added, and the mixture was stirred, to which 0.27 g of fumed silica (Cab-O-Sil M-7D, produced by Cabot Corporation) was added as a silica source, and further stirred sufficiently. Further, 0.0054 g of a BEA type borosilicate was added as a seed crystal, and the mixture was stirred to prepare a raw material gel.

The prepared raw material gel was charged into an autoclave and heated at 170° C. for 5 days with stirring at 40 rpm. The product was filtrated, washed with water, and then dried at 100° C. overnight. After drying, it was calcined in an air atmosphere at 600° C. for 6 hours to yield 0.201 g of a sodium type zeolite powder (borogermanosilicate).

(Removal of B and Ge, and Introduction of Al)

The post-treatment was carried out for the purpose of removing boron and germanium in the zeolite framework of the obtained borogermanosilicate and replacing them with aluminum. The post-treatment was carried out in the same manner as in Example 1 to obtain 0.162 g of a protonic zeolite powder (aluminosilicate).

2. Evaluation of Zeolite Catalyst (Aluminosilicate)

For the aluminosilicates according to Examples 1 to 6 and Comparative Examples 1 to 5, the following evaluations were carried out.

<Elemental Analysis>

Elemental analyses were carried out by inductively-coupled plasma atomic emission spectrometry (ICP-AES). For the analyses, an ICPE-9000 produced by Shimadzu Corporation was used. The compositions of the synthesized aluminosilicates in Examples 1 to 6 and Comparative Examples 1 to 5 are shown in Table 2.

<X-Ray Diffraction Analysis>

Figure 2:
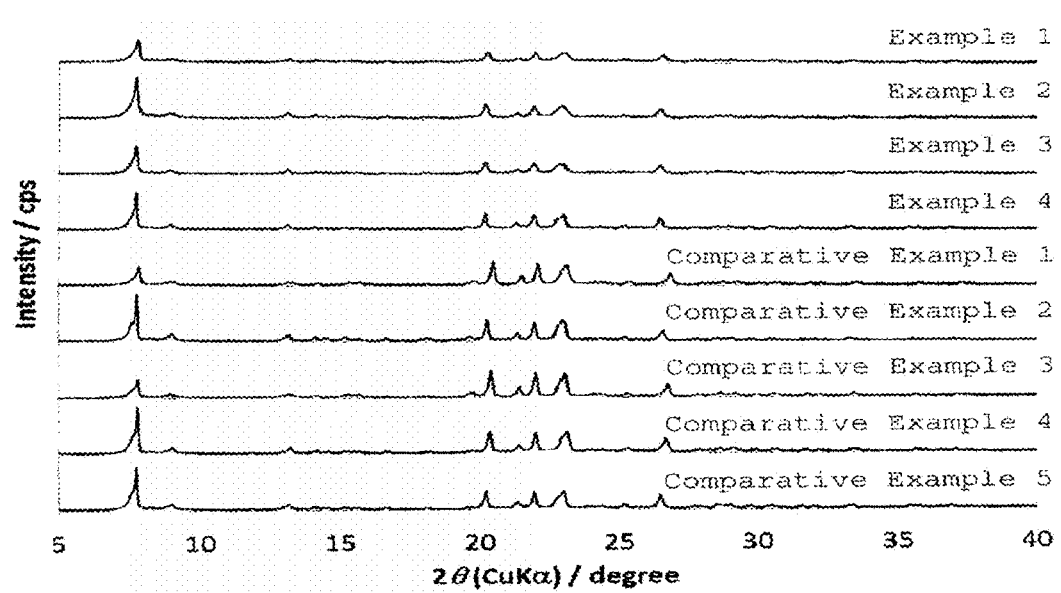
FIG. 2 is a chart showing powder X-ray diffraction results of the zeolite catalysts according to Examples 1 to 4, and Comparative Examples 1 to 5.
Figure 3:
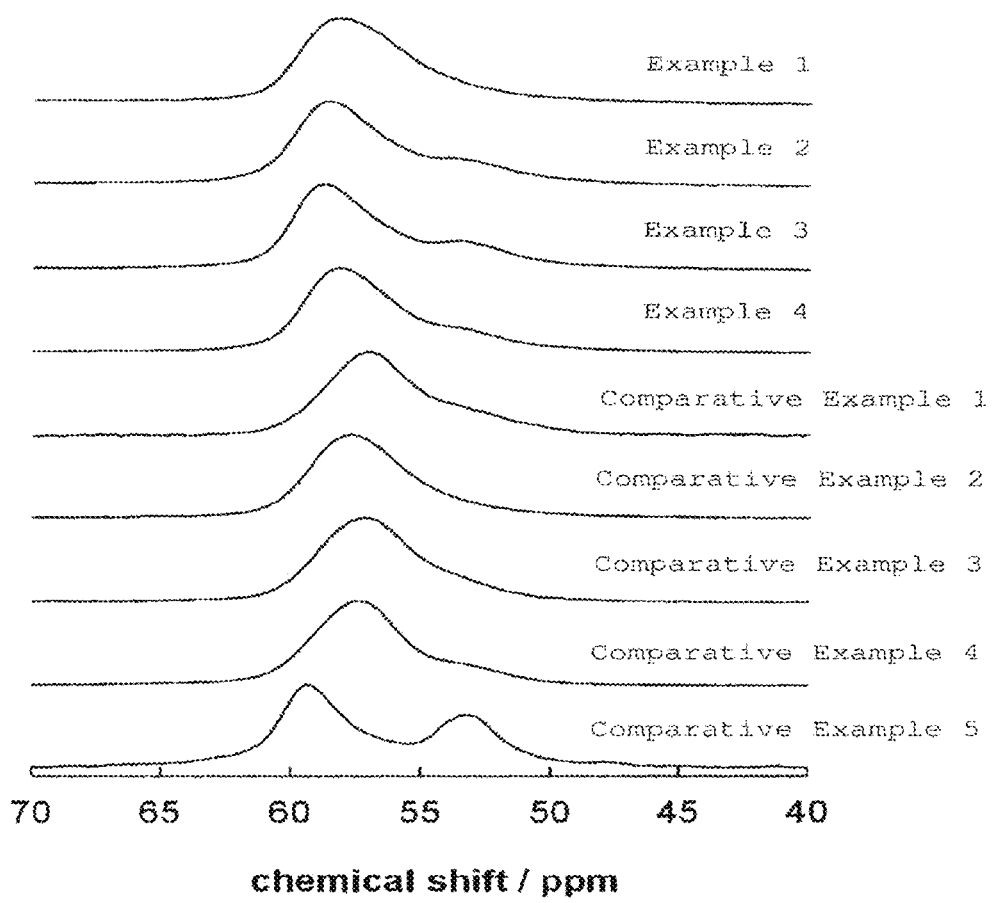
FIG. 3 is a chart showing $^{2}$Al-MAS-NMR spectra of the zeolite catalysts according to Examples and Comparative Examples.

X-ray diffraction (XRD) analyses of the synthesized aluminosilicate were carried out using a RINT Ultima III produced by Rigaku Corporation. The X-ray source was CuKα (X-ray output: 40 kV, 40 mA), the reading width was 0.02°, and the scanning speed was 20.0°/min. The XRD patterns obtained by analyses are shown in FIG. 2. It was confirmed from FIG. 2 that each aluminosilicate according to Examples 1 to 4 or Comparative Examples 1 to 5 was a zeolite having a CON framework.

Figure 5:
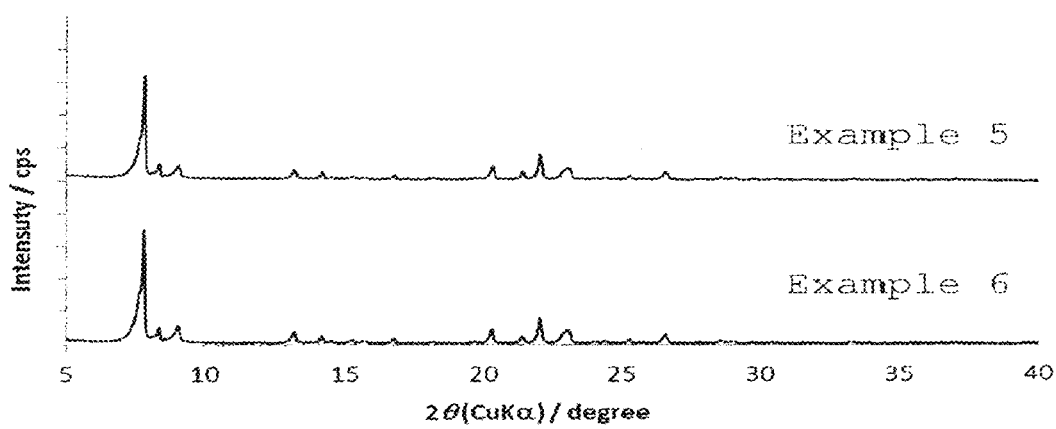
FIG. 5 is a chart showing powder X-ray diffraction results of the zeolite catalysts according to Examples 5 and 6.
Figure 6:
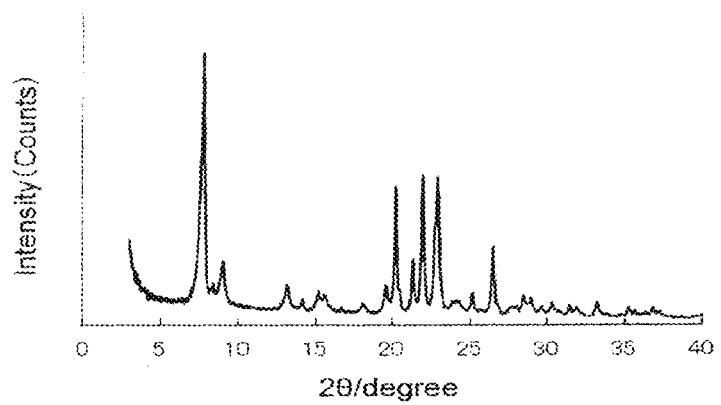
FIG. 6 is an XRD pattern of the CON zeolite obtained in Example A1.

The X-ray diffraction (XRD) analyses of the aluminosilicates according to Examples 5 and 6 were carried out using an X'PERT PRO MPD produced by Malvern Panalytical B. V. The X-ray source was CuKα (X-ray output: 40 kV, 30 mA), the reading width was 0.016°, and the scanning speed was 4.0°/min. The XRD patterns obtained by the analyses are shown in FIG. 5. It was confirmed from FIG. 5 that each of the aluminosilicate according to Examples 5 and 6 was a zeolite having a CON framework.

<Analysis of Half Width>

An X-ray diffraction (XRD) analysis for measuring a half width was carried out using an X'PERT PRO MPD produced by Malvern Panalytical B. V. The X-ray source was CuKα (X-ray output: 40 kV, 30 mA), the reading width was 0.016°, and the scanning speed was 4.0°/min. The "half width" of the peak of the (130) plane" and the "half width of the peak of the (510) plane" obtained from an XRD pattern obtained under the measurement conditions are shown in Table 2.

As obvious from Table 2, a sample having a smaller average primary particle diameter tends to have a larger half width. With respect to Comparative Example 2, although the average primary particle diameter is large, the half width is relatively large. This result is conceivably because particles partially containing polycrystals were included in the calculation of an average primary particle diameter with respect to this sample.

<$^{27}$Al-MAS-NMR>

An analysis of $^{27}$Al-MAS-NMR is carried out after placing a sample of aluminosilicate in a sample tube for NMR, leaving the same standing in a desiccator filled with a saturated aqueous solution of ammonium chloride overnight for absorbing moisture sufficiently, and then closing the tube hermetically, under the conditions shown in the following Table 1 using a 1.0 M aluminum chloride aqueous solution as a reference material (−0.10 ppm). With respect to the $^{27}$Al-MAS-NMR spectrum obtained by the analysis, the ratio (($A_2/A_1$)×100(%)) of the integrated intensity area ($A_2$) of the signal intensity in the range from 57.5 ppm to 70 ppm to the integrated intensity area ($A_1$) of the signal intensity in the range from 45 ppm to 70 ppm was calculated. The results are shown in Table 2.

TABLE 1

| Apparatus | Varian NMR Systems 400 WB produced by Agilent |
|---|---|
| Probe | Probe for CP/MAS: 4 mmφ T3HX |
| Observed nucleus | $^{27}$Al |
| Measurement method | Single Pulse method |
| Resonant frequency | 104.18 MHz |
| Pulse width | 1 μs (equivalent to 22.5° pulse) |

TABLE 1-continued

| MAS rotation speed | 12 kHz |
|---|---|
| Waiting time | 0.1 sec |
| Spectral width | 250 kHz |
| Measurement temperature | Room temperature |
| Cumulative number | 36000 times |
| Reference material | 1.0M aluminum chloride aqueous solution (−0.10 ppm) |

<Scanning Electron Microscope>

Figure 4:
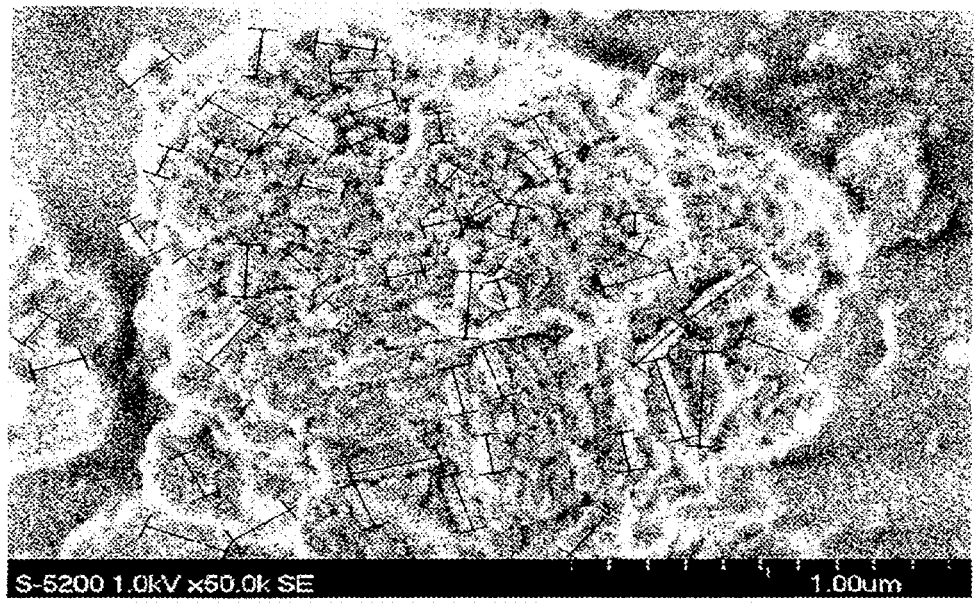
FIG. 4 is an SEM image of the zeolite catalyst according to Example 1.

A measurement with a scanning electron microscope (SEM) was carried out using an S-5200 produced by Hitachi High-Technologies Corporation. From the obtained SEM image, 50 primary particles were randomly extracted, and the major axis lengths of the particles were measured as the particle diameters. The arithmetic mean of the obtained particle diameters was defined as the average primary particle diameter. The results are shown in Table 2. For reference, FIG. 4 shows an SEM image of the zeolite catalyst according to Example 1. As shown in FIG. 4, in the zeolite catalyst according to Example 1, fine primary particles aggregate to form a secondary particle.

<Production of Lower Olefin>

Production of lower olefin was carried out using a CON zeolite catalyst obtained in Examples 1 to 6 and Comparative Examples 1 to 5.

For the reaction, a quartz reaction tube having an inner diameter of 4 mm was filled with 100 mg of each zeolite having a CON framework obtained in Examples 1 to 6 and Comparative Examples 1 to 5, using a normal pressure fixed bed flow reactor. A mixed gas of 50.0 mol % of methanol and 50.0 mol % of helium was supplied to the reactor, such that the weight hourly space velocity of methanol was 15 hr$^{-1}$, and a reaction was conducted at 450° C. and 0.1 MPa (absolute pressure). The product was analyzed by gas chromatography every 1 hour or 2 hours from the start of the reaction (with respect to Example 1 every 2 hours or 4 hours). The methanol conversion, and the ethylene selectivity, propylene selectivity, and butene selectivity after 2 hours from the start of the reaction are shown in Table 2. In this regard, a methanol conversion means herein a conversion of methanol alone without dimethyl ether. Further, the catalyst life $L_1$ and the catalyst life $L_2$ shown in Table 2 are defined respectively as the time periods in which the methanol conversion is maintained at 95% or more, or 90% or more.

TABLE 2

| | | Example 1 | Example 2 | Example 3 | Example 4 | Comparative Example 1 | Comparative Example 2 |
|---|---|---|---|---|---|---|---|
| Initial charge composition (molar ratio) | TMMAOH/Si | 0.2 | 0.2 | 0.2 | 0.2 | 0.2 | 0.2 |
| | NaOH/Si | 0.12 | 0.12 | 0.1 | 0.08 | 0.12 | 0.1 |
| | H$_2$O/Si | 30 | 30 | 30 | 20 | 30 | 60 |
| | H$_3$BO$_3$/Si | 0.2 | 0.1 | 0.04 | 0.04 | 0.2 | 0.04 |
| | (CH$_3$COO)$_2$Zn/Si | — | 0.005 | 0.01 | — | — | — |
| | GeO$_2$/Si | — | — | — | — | — | — |
| | Al$_2$(SO$_4$)$_3$/Si | — | — | — | 0.007 | 0.002 | — |
| | Seed/Si | 0.02 | 0.02 | 0.02 | 0.02 | 0.02 | 0.02 |
| Post-treatment composition (molar ratio) | H$_2$O/Si | 333 | 333 | 333 | 333 | — | 167 |
| | Al(NO$_3$)$_3$/Si | 0.0025 | 0.0025 | 0.0025 | 0.005 | — | 0.33 |
| Zeolite catalyst composition (molar ratio) | Si/Al | 399 | 276 | 289 | 109 | 228 | 99 |
| | Si/B | 389 | 3438 | n. d | 448 | 17 | 745 |
| | Si/Zn | — | 7798 | 7023 | — | — | — |
| | Si/Ge | — | — | — | — | — | — |
| Half width | (130) plane | 0.193 | 0.176 | 0.163 | 0.125 | 0.144 | 0.147 |
| | (510) plane | 0.193 | 0.198 | 0.171 | 0.122 | 0.163 | 0.139 |
| ($A_2/A_1$) × 100 (%) | | 51.3 | 54.6 | 54.4 | 50 | 32 | 47.5 |
| Average primary particle diameter (nm) | | 150 | 150 | 180 | 750 | 160 | 2900 |

TABLE 2-continued

| | | | | | | | |
|---|---|---|---|---|---|---|---|
| Methanol conversion (%) | 96.6 | 99.4 | 98.8 | 100 | 100 | 73.7 |
| Ethylene selectivity (mol %) | 2.5 | 3.3 | 3.2 | 5.2 | 2.9 | 1.9 |
| Propylene selectivity (mol %) | 49.3 | 50.2 | 48 | 46.1 | 54.7 | 20.7 |
| Butene selectivity (mol %) | 26.6 | 25.3 | 24.8 | 17.4 | 20 | 13.8 |
| Catalyst life $L_1$ (hr) | 24 | 26 | 24 | 6 | 20 | 1 |
| Catalyst life $L_2$ (hr) | 36 | 30≤*1 | 38≤*2 | 6 | 22 | 1 |

| | | Comparative Example 3 | Comparative Example 4 | Comparative Example 5 | Example 5 | Example 6 |
|---|---|---|---|---|---|---|
| Initial charge composition (molar ratio) | TMMAOH/Si | 0.2 | 0.2 | 0.2 | 0.2 | 0.2 |
| | NaOH/Si | 0.1 | 0.08 | 0.08 | 0.1 | 0.1 |
| | $H_2O$/Si | 30 | 20 | 20 | 30 | 30 |
| | $H_3BO_3$/Si | 0.04 | 0.04 | 0.04 | 0.04 | 0.04 |
| | $(CH_3COO)_2Zn$/Si | — | — | — | — | — |
| | $GeO_2$/Si | — | — | — | — | 0.06 |
| | $Al_2(SO_4)_3$/Si | 0.0025 | 0.007 | 0.007 | — | — |
| | Seed/Si | 0.02 | 0.02 | 0.02 | 0.02 | 0.02 |
| Post-treatment composition (molar ratio) | $H_2O$/Si | — | — | — | 333 | 333 |
| | $Al(NO_3)_3$/Si | — | — | — | 0.0025 | 0.0025 |
| Zeolite catalyst composition (molar ratio) | Si/Al | 192 | 84 | 297 | 262 | 246 |
| | Si/B | 24 | 26 | n. d. | 481 | n d. |
| | Si/Zn | — | — | — | — | — |
| | Si/Ge | — | — | — | — | 721 |
| Half width | (130) plane | 0.133 | 0.114 | 0.111 | 0.126 | 0.121 |
| | (510) plane | 0.141 | 0.117 | 0.12 | 0.125 | 0.117 |
| $(A_2/A_1) \times 100$ (%) | | 38.8 | 44 | 48.6 | 61.6 | 54.3 |
| Average primary particle diameter (nm) | | 360 | 660 | 820 | 570 | 940 |
| Methanol conversion (%) | | 100 | 99 | 96.7 | 99.6 | 99.1 |
| Ethylene selectivity (mol %) | | 4.2 | 7 | 3 | 3.3 | 3.3 |
| Propylene selectivity (mol %) | | 50.6 | 48.5 | 53.9 | 48.6 | 46.2 |
| Butene selectivity (mol %) | | 18.4 | 15.7 | 19.1 | 25.7 | 25.1 |
| Catalyst life $L_1$ (hr) | | 12 | 2 | 2 | 28 | 10 |
| Catalyst life $L_2$ (hr) | | 12 | 2 | 5 | 36 | 18 |

*1There is no data after 30 hr, but the conversion at 30 hr is 94.4%.
*2There is no data after 38 hr, but the conversion at 38 hr is 92.7%.

When the results of Examples 1 to 3, Example 5 and Comparative Examples 1 to 5 in Table 2 are compared, it is obvious that a zeolite, in which the ratio with respect to the integrated intensity areas $((A_2/A_1) \times 100(\%))$ is large, and the average primary particle diameter is small, has a long catalyst life. In the case of the zeolite of Examples 4 and 6, the average primary particle diameter is relatively large, and therefore the catalyst life is short compared to Examples 1 to 3, but the catalyst life is still longer compared to Comparative Examples 4 and 5 having almost equivalent average primary particle diameter. In the case of Example 5, it shows a lifetime comparable to Examples 1 to 3 despite a large average primary particle diameter. This is conceivably because the ratio with respect to the integrated intensity areas $((A_2/A_1) \times 100(\%))$ is larger than in Examples 1 to 3. The above means that the catalyst life of a zeolite having a high ratio with respect to the integrated intensity areas $((A_2/A_1) \times 100(\%))$ is long.

Next, other aspects of the present invention will be described.

Other aspects are as the following [1] to [10]. Hereinafter, "the present embodiment" refers to an embodiment of the inventions of [1] to [10].

[1] A CON zeolite satisfying the following (1) to (2).
 (1) The framework is CON as per the code specified by the International Zeolite Association (IZA).
 (2) It contains silicon and aluminum, and the molar ratio of aluminum to silicon is 0.04 or more.
[2] The CON zeolite according to [1] having a crystal of polymorph B.
[3] The CON zeolite according to [1] or [2], wherein the molar ratio of aluminum to silicon is higher than 0.08.
[4] A method of producing a zeolite of the type CON as per the code specified by the International Zeolite Association (IZA) by hydrothermal synthesis of a mixture containing a silicon source, an aluminum source, an alkali metal element source and/or an alkaline earth metal element source, an organic structure-directing agent, and water, wherein the molar ratio of aluminum to silicon in the mixture is higher than 0.01.
[5] The method of producing a CON zeolite according to [4], which is a method of producing a zeolite having a crystal of polymorph B.
[6] The method of producing a CON zeolite according to [4] or [5], wherein the molar ratio of aluminum to silicon in the mixture is 0.08 or more.
[7] A CON zeolite obtained by the method of producing a CON zeolite according to any one of [4] to [6].
[8] A catalyst for producing a lower olefin or an aromatic hydrocarbon containing the CON zeolite according to any one of [1] to [3], or [7].
[9] An adsorbent containing the CON zeolite according to any one of [1] to [3], or [7].
[10] An exhaust gas treatment catalyst containing the CON zeolite according to any one of [1] to [3], or [7].

The present embodiment relates to a method of producing a CON zeolite having a high aluminum content, and a CON zeolite, which is produced by the method, and has higher catalytic performance and stability than the case where it is synthesized in two stages using a conventional main raw material of boron, as well as a use of the same.

Zeolite has characteristics, such as molecular sieve effect, ion exchange ability, catalytic ability, and adsorption ability due to pores derived from its framework structure, and is currently widely used as an adsorbent, an ion exchanger, an industrial catalyst, and an environmental catalyst.

The CON zeolite is one of zeolites having pores of 10-membered oxygen ring and two types of 12-membered oxygen rings, and has a topology which is classified as CON as per the framework code defined by the International Zeolite Association (hereinafter occasionally abbreviated as "IZA"). Since the CON zeolite has large pores of different sizes, it is expected as a catalyst for producing a lower olefin and an aromatic, an adsorbent, and an exhaust gas treatment catalyst.

As a CON zeolite CIT-1 ([B]—CON) and SSZ-33 ([B]—CON) as a borosilicate, SSZ-26 ([Al]—CON) as an aluminosilicate, and ITQ-24 ([Ge]—CON) as a germanosilicate have been known.

CIT-1 is a CON zeolite containing boron as a main component, which is composed of a single component of polymorph B. As a general production method, U.S. Pat. No. 5,512,267 discloses a basic method, and as a specific production method, a zeolite CIT-1 containing boron ($Si/B_2$ ratio=50) is yielded by conducting a hydrothermal synthesis at 175° C. for 7 days using fumed silica and sodium borate as raw materials, N,N,N-trimethyl-cis-myrtanylammonium hydroxide as an organic structure-directing agent, and NaOH as an alkali source. U.S. Pat. No. 5,512,267 claims that synthesis is possible to introduce silicon, germanium, aluminum, gallium, iron, titanium, vanadium, or a mixed composition thereof as a T atom, however in fact substantially all Examples were related to [B]—CON containing silicon and boron as main components. In a synthesis of [Al]—CON containing aluminum in Example, a technique, by which [B]—CON was first synthesized and then aluminum was introduced by ion exchange in an aluminum nitrate aqueous solution, was used.

Am. Chem. Soc. Catal., 5, 4268 (2015), Japanese Unexamined Patent Application Publication No. 2013-245163 disclose a direct production method by a hydrothermal synthesis of boroaluminosilicate containing boron as well as a small amount of aluminum. Specifically, according to the disclosure, [B, Al]—CON having a $Si/B_2$ ratio from 50 to 74 and a $Si/Al_2$ ratio from 218 to 310 may be produced by using boron as a main component at a $Si/B_2$ ratio of 50, then adding aluminum sulfate, and performing a hydrothermal synthesis at a $Si/Al_2$ ratio from 200 to 400. However, there has been presented data showing that [B, Al]—CON cannot be produced with a composition of a $Si/Al_2$ ratio less than 200. As evidenced by this fact, it is a common technical knowledge which has been established through the 20 year history of CIT-1, that CIT-1 is a zeolite which can be synthesized only when boron is a main component.

SSZ-33 is a CON zeolite containing boron as a main component similarly to CIT-1, however it is an intergrowth of polymorphs A/B (70:30) with different layering modes. The production method is disclosed in U.S. Pat. No. 4,963,337, and it is so described that a borosilicate having a $Si/B_2$ ratio from 30 to 50 may be synthesized by performing synthesis using fumed silica and sodium borate as raw materials, and N,N,N-trimethyltricyclo[5.2.1.0$^{2,6}$]decane ammonium hydroxide as an organic structure-directing agent. Similarly, to CIT-1, introduction of aluminum in Example was carried out after yielding a borosilicate by hydrothermal synthesis, by ion exchange in an aluminum nitrate aqueous solution.

Meanwhile, SSZ-26 is a CON zeolite containing aluminum as a main component, but it is an intergrowth of polymorphs A/B (85:15) with different layering modes. A production method thereof is disclosed in U.S. Pat. No. 4,910,006, and specifically by performing synthesis using fumed silica, zeolite Y as raw materials, and hexamethyl [4.3.3.0]propellane-8,11-diammonium cation as an organic structure-directing agent, an aluminosilicate having a $Si/Al_2$ ratio from 25 to 35 is obtained.

Also, ITQ-24 is a CON zeolite containing germanium as a main component, which is composed of a single component of polymorph C with a layering mode different from CIT-1. A production method thereof is disclosed in J. Am. Chem. Soc., 125, 7820 (2003), and specifically by performing hydrothermal synthesis at 175° C. for 15 days using tetraethoxysilane, germanium oxide, and aluminum isopropoxide as raw materials, and adding hexamethonium hydroxide as an organic structure-directing agent to obtain [Ge, Al]—CON ($Si/Ge_2$=10, $Si/Al_2$=37) containing silicon as well as germanium as main components.

As mentioned above, examples of a zeolite having a CON framework include CIT-1, SSZ-26, SSZ-33, and ITQ-24, but they are treated as different materials characterized by the respective XRD patterns, because they are different not only in constituent elements but also in polymorph properties.

However, the aforedescribed known methods have various drawbacks, and fully satisfactory results have not been obtained.

Since a CON zeolite (CIT-1) containing silicon and boron as main components was produced by the method disclosed in U.S. Pat. No. 5,512,267, Japanese Unexamined Patent Application Publication No. 2013-245163, and Am. Chem. Soc. Catal., 5, 4268 (2015), in order to yield a CON zeolite with a high aluminum content, it was necessary to go through two steps, namely to synthesize borosilicate at first, and then to introduce aluminum by a subsequent post-treatment. Therefore, there was a drawback in that the production cost became high. Further, there was an upper limit of the boron content in a borosilicate ($Si/B_2$ molar ratio of about 50), and there was a drawback in that it was not possible to introduce more aluminum into the framework. In addition, Al insertion into the zeolite framework may be incomplete, and aluminum species outside the framework tends to increase, and a zeolite, in which aluminum species is instable, tends to be yielded.

Further, since a CON zeolite (SSZ-33) containing silicon and boron as main components similar to the aforedescribed CIT-1 was produced by the method disclosed in U.S. Pat. No. 4,963,337, in order to yield a CON zeolite with a high aluminum content, two production steps of a hydrothermal synthesis step and a post-treatment step were required. Further, there was an upper limit of the introduction amount of aluminum. In addition, there was a drawback in that an organic structure-directing agent to be used had a very sophisticated structure and was very expensive, forcing the production cost to become high. Further, there was another drawback in that the crystal structure defined by the organic structure-directing agent inevitably became a mixed crystal of polymorphs A/B.

Since a CON zeolite (SSZ-26) containing silicon and aluminum as main components was produced by the method disclosed in U.S. Pat. No. 4,910,006, a CON zeolite having a relatively high aluminum content may be produced. However, there was a drawback in that the introduction amount of aluminum in terms of the $Si/Al_2$ ratio was limited to a narrow range of 25 to 35. Further, similarly to SSZ-33, an organic structure-directing agent to be used had a very sophisticated structure and was very expensive, and therefore the production cost became high. Further, there was another drawback in that the crystal structure defined by the organic structure-directing agent inevitably became a mixed crystal of polymorphs A/B.

Since a CON zeolite (ITQ-24) containing silicon and germanium as main components was produced by the method disclosed in *J. Am. Chem. Soc.*, 125, 7820 (2003), the introduction amount of aluminum was limited, and a large amount of germanium species susceptible to hydrolysis was contained, there was another drawback in that the framework was instable.

An object of another aspect of the present invention is to provide a method of producing a CON zeolite having a high aluminum content in one step by hydrothermal synthesis, a CON zeolite, which is produced by the method and has a catalytic performance higher than the conventional CON zeolite, and a catalyst composed of the CON zeolite. In addition, an object of another aspect of the present invention is to provide a method of producing a CON zeolite capable of widely and freely adjusting the Al content, and further to provide a CON zeolite having an Al/Si ratio of 0.04 or higher.

As a result of extensive studies by the inventors of the present invention for achieving the objects, it has been found that by regulating the ratio of silicon to aluminum in a raw material mixture for hydrothermal synthesis within a specific range, a CON zeolite having a high aluminum content, which has not been present heretofore, may be obtained, and even in high yield; that the CON zeolite produced by this method is superior in terms of catalytic activity and adsorption property to an [Al]—CON zeolite, which has introduced aluminum by a post-treatment of a conventional [B]—CON zeolite containing boron as a main component; and that a CON zeolite having any Al/Si ratio, including a CON zeolite having an Al/Si ratio of 0.04 or higher, may be produced; thereby accomplishing such aspect of the present invention.

By another aspect of the present invention, a CON zeolite having a high aluminum content may be produced by a single step hydrothermal synthesis without using an expensive structure-directing agent. Moreover, a CON zeolite having a high aluminum content obtained according to another aspect of the present invention is superior in catalytic activity and adsorption property to a conventional CON zeolite synthesized in two steps using boron as a main raw material, and may be used favorably as a catalyst for producing a lower olefin and an aromatic, an adsorbent, and a catalyst for an exhaust gas treatment, and especially as an adsorbent for hydrocarbons. Further, by the production method of another aspect of the present invention, a CON zeolite having an Al/Si ratio of 0.04 or higher may be produced, and when this is used as an adsorbent for hydrocarbons, it may function as an adsorbent having superior adsorption performance. Further, the Al content of an obtained CON zeolite may be adjusted widely.

Representative modes for implementing another aspect of the present invention will be described specifically below. However, other aspects of the present invention are not limited to the following modes insofar as not departing from the scope and spirit of this invention, and various modifications are possible.

Another aspect of the present invention (hereinafter also referred to as the present embodiment) will be described in detail below.

1. CON Zeolite of the Present Embodiment
(Structure)

A zeolite of the present embodiment has a CON framework. Regarding the CON zeolite, it is the same as the first embodiment described above.

Its structure may be characterized by X-ray diffraction data. However, when an actually prepared zeolite is measured, since it has been affected by the growth direction of zeolite, the ratios among constituent elements, adsorbed substances, presence of defects, drying condition, etc., the relative intensity, and the peak position of each peak may fluctuate slightly. Therefore, it is not possible to reproduce exactly the same values as the parameters of the CON framework set forth in the IZA specifications, and there is tolerance of about 10%.

With respect to the relative intensity and the peak position of each peak of a CON zeolite of the first embodiment, there is also tolerance of about 10%.

A CON zeolite of the present embodiment may have a crystal of polymorph B or may be a single crystal of polymorph B. The crystal of polymorph B is, for example, a crystal having an interplanar spacing d (Å) shown in the following Tables 3A and 3B (Table 3A: a state including an organic structure-directing agent, and Table 3B: a state not including an organic structure-directing agent). With respect to the interplanar spacing, difference of ±0.3° in terms of 2θ and ±2% in terms of each interplanar spacing d may be tolerated, from the values in Tables 3A and 3B, depending on difference in a production method, etc. The method of measuring an interplanar spacing is as described in Examples below. Among the interplanar spacings in Table 3A, principal interplanar spacings d for identifying CIT-1 which is a crystalline form of polymorph B are: 9.86 Å (9.77), 6.26 Å (6.26), 5.84 Å (5.79), 5.67 Å (5.68), 4.91 Å (4.88), 4.54 Å (4.51), 3.73 Å (3.72), and 3.68 Å (3.66) (numerical values in parentheses are values in a state not including an organic structure-directing agent in Table 3B) For a CON zeolite of the present embodiment, at least 6, preferably 7 or more, and more preferably all of 8 out of 8 spacings are agreed. Further, at least 85%, preferably 90% or more, and more preferably 95% or more of all the interplanar spacing shown in Tables 3A and 3B are agreed.

There is no particular restriction on the content of polymorph B in a CON zeolite of the present embodiment, and it may be 25% or more, 50% or more, 75% or more, or 100% on a weight basis.

[Table 3A]

TABLE 3A

| 2θ (°) [a] | d (Å) | Relative Intensity [I/Io × 100] |
|---|---|---|
| 7.74 | 11.41 | Extremely strong |
| 8.35 | 10.58 | Weak |
| 8.96 | 9.86 | Weak |
| 13.14 | 6.73 | Weak |
| 14.14 | 6.26 | Weak |
| 15.17 | 5.84 | Weak |
| 15.63 | 5.67 | Weak |
| 16.67 | 5.31 | Extremely weak |
| 18.04 | 4.91 | Extremely weak |
| 19.56 | 4.54 | Weak |
| 20.20 | 4.39 | Moderate |
| 21.27 | 4.17 | Weak |
| 21.90 | 4.06 | Moderate |
| 22.86 | 3.89 | Moderate |
| 23.83 | 3.73 | Weak |
| 24.20 | 3.68 | Weak |
| 25.07 | 3.55 | Weak |

TABLE 3A-continued

| 2θ (°)[a] | d (Å) | Relative Intensity [I/Io × 100] |
|---|---|---|
| 26.46 | 3.37 | Moderate |
| 27.66 | 3.22 | Extremely weak |
| 27.96 | 3.19 | Extremely weak |
| 28.59 | 3.12 | Weak |
| 28.90 | 3.09 | Weak |
| 29.59 | 3.02 | Extremely weak |
| 30.25 | 2.95 | Extremely weak |
| 30.78 | 2.90 | Extremely weak |
| 31.43 | 2.84 | Extremely weak |
| 31.84 | 2.81 | Extremely weak |
| 33.13 | 2.70 | Extremely weak |
| 35.25 | 2.54 | Extremely weak |
| 35.65 | 2.52 | Extremely weak |
| 36.82 | 2.44 | Extremely weak |
| 37.17 | 2.42 | Extremely weak |

[a] (±0.3)

[Table 3B]

TABLE 3B

| 2θ (°)[a] | d (Å) | Relative Intensity [I/Io × 100] |
|---|---|---|
| 7.77 | 11.36 | Extremely strong |
| 8.35 | 10.58 | Weak |
| 9.04 | 9.77 | Weak |
| 13.19 | 6.71 | Weak |
| 14.14 | 6.26 | Weak |
| 15.30 | 5.79 | Extremely weak |
| 15.60 | 5.68 | Extremely weak |
| 16.70 | 5.30 | Extremely weak |
| 18.16 | 4.88 | Extremely weak |
| 19.69 | 4.51 | Extremely weak |
| 20.25 | 4.38 | Weak |
| 21.37 | 4.15 | Weak |
| 21.95 | 4.05 | Weak |
| 23.07 | 3.85 | Moderate |
| 23.93 | 3.72 | Extremely weak |
| 24.32 | 3.66 | Extremely weak |
| 25.25 | 3.52 | Weak |
| 26.52 | 3.36 | Weak |
| 27.73 | 3.22 | Extremely weak |
| 28.53 | 3.13 | Extremely weak |
| 28.93 | 3.08 | Weak |
| 29.64 | 3.01 | Extremely weak |
| 30.45 | 2.93 | Extremely weak |
| 31.51 | 2.84 | Extremely weak |
| 33.32 | 2.69 | Extremely weak |
| 35.45 | 2.53 | Extremely weak |
| 35.71 | 2.51 | Extremely weak |
| 36.90 | 2.43 | Extremely weak |

[a] (±0.3)

In this regard, the relationship between the XRD relative intensity in above Tables and the value of an XRD peak expressed by I/Io×100 in the actual XRD pattern is as shown in the following Table 3C below. In Tables 3A and 3B above, I and $I_0$ have the following meanings:

I: X-ray diffraction intensity at each interplanar spacing d
$I_0$: The maximum XRD peak intensity in the XRD pattern

[Table 3C]

TABLE 3C

| XRD relative intensity | Relative Intensity [I/$I_0$ × 100] |
|---|---|
| Extremely strong | not less than 90 |
| Strong | not less than 70 and less than 90 |
| Moderate | not less than 30 and less than 70 |
| Weak | not less than 10 and less than 30 |
| Extremely weak | less than 10 |

(Constituent Component)

A CON zeolite of the present embodiment contains aluminum as a component other than silicon and oxygen, and contains 90 mol % s or more of silicon atoms and aluminum atoms in the T atoms. In addition, at least one element M selected from boron, gallium, and iron (hereinafter simply referred to as "element M") may be contained in the T atoms.

Since a zeolite of the present embodiment includes aluminum as a main component in addition to silicon in the T atoms, it develops an active site with a high acid strength and functions as an active site for a conversion reaction of methanol or a hydrocarbon. Therefore, it is superior in catalytic performance. When it is used as an adsorbent for a hydrocarbon, etc., it is preferable that the content of aluminum is high, because the adsorption capacity may be larger, and the desorption temperature tends to be higher. Also, when it is used as an SCR catalyst for a treatment of an exhaust gas of an automobile, etc., a catalyst with a higher aluminum content is superior in the efficiency of exhaust gas treatment especially during an operation at a low temperature at the start.

As a zeolite of the present embodiment, an aluminosilicate, in which the T atoms are composed of silicon and aluminum, a boroaluminosilicate, a galloaluminosilicate, a ferrialuminosilicate, a borogalloaluminosilicate, and a boroferrialuminosilicate are preferable; an aluminosilicate, a boroaluminosilicate, and a ferrialuminosilicate are more preferable; and an aluminosilicate, in which the T atoms are composed of silicon and aluminum, and a boroaluminosilicate composed of silicon, aluminum and boron are further preferable.

A zeolite of the present embodiment may contain additional elements other than the above elements. Examples of other elements include, but not limited to, zinc (Zn), germanium (Ge), titanium (Ti), zirconium (Zr), and tin (Sn). These constituent elements may be used singly, or in a combination of two or more types.

(Molar Ratio of Aluminum to Silicon)

The molar ratio (Al/Si) of aluminum to silicon in a zeolite of the present embodiment is usually 0.01 or more, preferably 0.02 or more, more preferably 0.04 or more, further preferably 0.05 or more, and especially preferably higher than 0.08; and is usually 0.30 or less, preferably 0.20 or less, more preferably 0.15 or less, further preferably 0.13 or less, and especially preferably 0.10 or less. When the Al/Si molar ratio falls within the above range, a sufficient quantity of acid sites having a high acid strength may be obtained, and in a conversion reaction of an organic compound raw material, a high adsorption ability for an organic compound, a high conversion activity, and olefin interconversion activity are obtained. Further, it is possible to prevent phenomena, such as deactivation of the catalyst by coking, desorption of T atoms other than silicon from the framework, and decrease in acid strength per acid site. Also, in a case in which the zeolite is used as an adsorbent, when the Al/Si molar ratio is within the above range, the number of adsorption sites derived from Al increases so that a high adsorption ability is obtained. Furthermore, due to the high adsorption ability, the desorption temperature becomes higher, and desorption at a low temperature may be suppressed. For example, in a case in which the zeolite is used as an adsorbent for a hydrocarbon, etc., especially as an adsorbent for adsorbing hydrocarbons emitted from an automobile engine (a hydrocarbon trapping material), the same is able to adsorb and retain a large amount of emitted hydrocarbon components during a cold start of an internal combustion engine (in a low temperature period). Also, in a case in which the zeolite is used as an SCR catalyst, when the Al/Si molar ratio is within the above range, it has advantageously a high purification performance on an exhaust gas containing nitrogen oxides owing to a large number of active sites as a catalyst. For example, in a truck, since it is used as an SCR catalyst in an atmosphere of a gas containing water vapor at a relatively low temperature of 700° C. or less, removal of Al from the framework by a water vapor hardly proceeds. As a result, the purification performance of an exhaust gas containing nitrogen oxides is given priority, and use of a zeolite having a large number of active sites in the zeolite framework, namely a zeolite having a high Al/Si molar ratio is desired. On the other hand, a zeolite having a small Al/Si molar ratio has an advantage in that the structure is not easily collapsed even in a high temperature gas atmosphere containing water vapor because the amount of Al in the zeolite framework is small. In the case of a diesel passenger car or a gasoline-powered car, since the zeolite is used as an SCR catalyst in an atmosphere of a gas containing water vapor at 800° C. or higher, high steam resistance is required. Therefore, it is desirable to use a zeolite having a small Al/Si molar ratio. In this regard, a CON zeolite having an Al/Si molar ratio of 0.04 or more has never been obtained in the past, and the same is a novel material. Considering all the foregoing together, the Al/Si molar ratio is preferably from 0.04 to 0.13, and more preferably from 0.05 to 0.10 for suppressing the effect of elimination of Al from the framework, and obtaining a high catalytic performance and an adsorption performance for a conversion reaction of an organic compound raw material, an adsorbent, and an exhaust gas treatment catalyst.

(Molar Ratio of Boron to Silicon)

The molar ratio (B/Si) of boron to silicon in a zeolite of the present embodiment is usually 0 or more, preferably 0.00002 or more, more preferably 0.0002 or more, further preferably 0.0004 or more, and especially preferably 0.0008 or more; and is usually 0.04 or less, preferably 0.02 or less, more preferably 0.008 or less, further preferably 0.004 or less, and especially preferably 0.002 or less. Since aluminum is generally less apt to be eliminated from the framework than boron, when the B/Si molar ratio falls within the above range, it is preferable that the B/Si molar ratio is low, namely that the boron content is relatively reduced, because the structural destruction due to elimination from the framework may be suppressed.

(Molar Ratio of Boron to Aluminum)

There is no particular restriction on the content of boron in the crystals of a zeolite of the present embodiment, and it is preferably low, namely the molar ratio of boron to aluminum (B/Al) is usually 1.0 or less, preferably 0.2 or less, more preferably 0.02 or less, further preferably 0.002 or less, and especially preferably 0.0002 or less. In general aluminum is less apt to be eliminated from the framework than boron, therefore it is preferable that the B/Al molar ratio is low, namely that the boron content is relatively reduced, because the structural destruction due to elimination from the framework may be suppressed.

The contents of Si, Al, and M (B, Fe, and Ga) in a zeolite of the present embodiment may be measured usually by ICP elemental analysis or fluorescent X-ray analysis. In the fluorescent X-ray analysis, a calibration curve is prepared between the fluorescent X-ray intensity of a test element in a reference sample and the atomic concentration of the test element, and the contents of silicon atoms, aluminum, gallium, and iron atoms in a zeolite sample may be determined by the X-ray fluorescence analysis (XRF) using the calibration curve. However, since the intensity of the fluorescent X-ray of the boron element is relatively weak, it is preferable to measure the content of the boron atom by an ICP element analysis.

(Fluorine Content)

Although there is no particular restriction on the content of fluorine in the crystal of a zeolite of the present embodiment, it is preferably as low as possible, usually 5000 ppm or less, preferably 1000 ppm or less, more preferably 100 ppm or less, and most preferably 0 ppm. By adjusting the fluorine content in the zeolite crystal within the above range, a sufficient specific surface area may be obtained, further, high diffusivity of a hydrocarbon component in the crystal may be obtained, and the conversion activity for an organic compound raw material may be enhanced.

(Total Acid Content)

The total acid content of a zeolite of the present embodiment (hereinafter referred to as "total acid content") is a sum total of the number of acid sites present in pores of the crystal of the zeolite and the number of acid sites on the outer surface of the crystal of the zeolite (hereinafter referred to as the outer surface acid content). Although there is no particular restriction on the total acid content, it is usually 0.10 mmol/g or more, preferably 0.30 mmol/g or more, more preferably 0.40 mmol/g or more, further preferably 0.50 mmol/g or more, and especially preferably 0.60 mmol/g or more. Also, it is usually 1.5 mmol/g or less, preferably 1.2 mmol/g or less, more preferably 1.0 mmol/g or less, further preferably 0.90 mmol/g or less, and especially preferably 0.80 mmol/g or less. By adjusting the total acid content within the above range, the conversion activity of an organic compound raw material may be secured, and coking generation of coke inside pores of a zeolite is inhibited so that the diffusibility of a molecule in the crystal may be maintained, which is preferable. In a case in which the zeolite is used as an adsorbent, when the total acid content is within the above range, the number of adsorption sites increases, so that a high adsorption ability may be obtained. Also, in a case in which the same is used as an SCR catalyst, the number of catalytic active site increases, so that it has advantageously high purification performance for an exhaust gas containing nitrogen oxides.

In this regard, the total acid content may be calculated from the desorbed amount in ammonia temperature-programmed desorption ($NH_3$-TPD). Specifically, a zeolite is dried in vacuum at 500° C. for 30 min as a pretreatment, and then the pre-treated zeolite is brought into contact with an excess amount of ammonia at 100° C. to adsorb ammonia thereon. The obtained zeolite is dried in vacuum at 100° C. (or brought into contact with steam at 100° C.) to remove excessive ammonia from the zeolite. Next, the zeolite having adsorbed ammonia is heated in a helium atmosphere at a temperature elevation rate of 10° C./min, and the desorbed amount of ammonia is measured by mass spectrometry from 100° C. to 600° C. The desorption amount of ammonia per weight of zeolite is deemed as the total acid content. However, the total acid content in the present embodiment is defined as the sum of the areas of the waveforms having its peak top at 240° C. or higher after waveform separation of the TPD profile by Gaussian functions. The "240° C." is an index used only for judgment of the position of a peak top, but not for calculating only the area of the portion of 240° C. or higher. Insofar as a waveform has its peak top at 240° C. or higher, the "waveform area" means the total area including the portion not higher than 240° C. In the case where there are a plurality of waveforms having a peak top at 240° C. or higher, the respective areas are summed up.

The total acid content according to the present embodiment does not include the acid content derived from a weak acid site having a peak top below 240° C. This is because it is not easy to distinguish between adsorption derived from a weak acid site and physical adsorption in the TPD profile.
(Outer Surface Acid Content)

Although there is no particular restriction on the acid content on the crystal outer surface of a zeolite of the present embodiment, it is usually 10% or less with respect to the total acid content of the zeolite, preferably 8% or less, and more preferably 5% or less. When the acid content on the outer surface is too high, it becomes difficult to obtain the shape selectivity unique to zeolite pores due to a side reaction occurring at the acid site on the outer surface, and the selectivity tends to decrease. There is no particular restriction on a method for adjusting the acid content on the outer surface of the zeolite, and examples thereof include silylation, steam treatment, and heat treatment of the outer surface of the zeolite. Further, there is a method, by which a binder and the acid site on the outer surface of the zeolite are bonded together in forming the zeolite.

An acid content on the outer surface may be calculated from the amount of a probe molecule (desorbed amount) per catalyst weight, when a probe molecule, which is too large to enter the pores of a zeolite, such as 4-propylquinoline, and 4-butylquinoline, is made to be adsorbed to an acid site on the zeolite surface, and then the adsorbed molecule is made to be desorbed from the catalyst by temperature increase. Specifically, for an acid content on the outer surface, a zeolite is dried at 500° C. in vacuum for 1 hour in a pre-treatment, then brought in contact with a vapor of probe molecules under a reduced pressure condition at 200° C. to 240° C., and an excessive amount of probe molecules is removed by evacuation and purging with helium at 200° C. to 240° C., the obtained zeolite is heated in a helium atmosphere at a temperature elevation rate of 10° C./min, and the desorbed amount of the probe molecules from 100° C. to 600° C. is measured by mass spectrometry. However, the acid content on the outer surface according to the present embodiment is defined similarly to the total acid content, as the sum of the areas of the waveforms having its peak top at 240° C. or higher after waveform separation of the TPD profile by Gaussian functions.
(Ion Exchange Site)

There is no particular restriction on the ion exchange site of a zeolite of the present embodiment. Usually, it is a proton (hereinafter also referred to as "protonic" or "H type") or partly a metal ion of an alkali metal such as lithium (Li), sodium (Na), potassium (K), and cesium (Cs); an alkaline earth metal such as magnesium (Mg), calcium (Ca), strontium (Sr), and barium (Ba); or the like. The ion exchange site is preferably a proton, sodium, potassium, or calcium, more preferably proton, sodium, and potassium, further preferably proton, and sodium, and especially preferably proton from the viewpoint of improvement of molecular diffusivity by decreasing the space occupied by a metal in the pore space. Hereinafter, for example, that exchanged with a Na ion is sometimes referred to as "Na type". That ion-exchanged with an ammonium ($NH_4$) is usually treated equivalently as a protonic type, because ammonia is eliminated therefrom under reaction conditions at a high temperature.
(Content of Alkali Metal/Alkaline Earth Metal)

Although there is no particular restriction on the total content of an alkali metal and an alkaline earth metal in a zeolite of the present embodiment, it is usually 0.005 mass % or more, preferably 0.01 mass % or more, more preferably 0.1% mass % or more, and further preferably 0.5 mass % or more; and is usually 10 mass % or less, preferably 5 masse or less, more preferably 3 mass % or less, and further preferably 1 mass % or less. By adjusting the total content of an alkali metal and an alkaline earth metal within the above range, the acid content, or the pore-space volume of a zeolite may be adjusted, so that accumulation of coke during the reaction may be advantageously suppressed. Further, the thermal/hydrothermal stability is improved, and deterioration may be suppressed, which is also advantageous.
(Average Primary Particle Diameter)

Although there is no particular restriction on the average primary particle diameter of a zeolite of the present embodiment, it is usually 0.03 μm or more, preferably 0.05 m or more, more preferably 0.1 μm or more, further preferably 0.15 μm or more, and especially preferably 0.20 μm or more; and is usually 5 μm or less, preferably 2 μm or less, more preferably 1 μm or less, further preferably 0.60 μm or less, and especially preferably 0.40 μm or less. By adjusting the primary particle diameter within the above range, the diffusibility in a zeolite crystal during a catalytic reaction and the effectiveness factor of catalyst may be sufficiently high, the zeolite crystallinity may be sufficient, and the hydrothermal stability may be high, which is preferable.

An average primary particle diameter in the present embodiment corresponds to the particle diameter of the smallest particle which grain boundary is not recognizable. Therefore, it is different from the particle diameter of an aggregate to be measured by the light scattering method, or the like. An average particle diameter is determined by measuring optional 50 or more particles through observation with a scanning electron microscope (hereinafter abbreviated as "SEM"), or a transmission electron microscope (hereinafter abbreviated as "TEM"), and averaging the particle diameters of the primary particles. The particle diameter was defined as the diameter (equivalent circle diameter) of a circle having an area equal to the projected area of the particle.

In this regard, it is not necessary for primary particles to be present as independent particles in the present embodiment, and they may form a secondary particle by aggregation or otherwise. Even if a secondary particle is formed, it is possible to distinguish primary particles on the surface of a secondary particle in the SEM or TEM image.

(BET Specific Surface Area)

Although there is no particular restriction on the BET specific surface area of a zeolite of the present embodiment, it is usually 300 m$^2$/g or more, preferably 400 m$^2$/g or more, and more preferably 500 m$^2$/g or more; and is usually 1000 m$^2$/g or less, preferably 800 m$^2$/g or less, and more preferably 750 m$^2$/g or less. Within the above range, the number of active sites present on the inner surfaces of pores is sufficiently large so that the catalytic activity may be enhanced advantageously. A BET specific surface area may be measured by a measuring method according to JIS 8830 (Determination of the specific surface area of powders (solids) by gas adsorption). A BET specific surface area may be obtained by the one point method (relative pressure: $p/p_0$=0.30) using nitrogen as the adsorption gas.

(Pore Volume)

Although there is no particular restriction on the pore volume of the zeolite of the present embodiment is not particularly limited, it is usually 0.10 mL/g or more, preferably 0.15 mL/g or more, and more preferably 0.20 mL/g or more; and is usually 0.50 mL/g or less, preferably 0.40 mL/g or less, and more preferably 0.35 mL/g or less. Within the above range, the number of active sites present on the inner surfaces of pores is sufficiently large so as to promote adsorption of a hydrocarbon component and to enhance advantageously the catalytic activity. The pore volume is preferably a value determined from the adsorption isotherm of nitrogen obtained by the relative pressure method.

($^{29}$Si-NMR)

The fact that the CON zeolite of the present embodiment is superior in crystallinity is also indicated by that the difference between the Si/Al$_2$ ratio of the bulk and the Si/Al$_2$ ratio obtained by $^{29}$Si-NMR after calcination is small. In other words, the Si/Al$_2$ ratio obtained by an elemental analysis of the calcined CON zeolite is the Si/Al$_2$ ratio of the bulk containing silicon and aluminum in the portion where the framework is broken during hydrothermal synthesis or calcination, meanwhile, the Si/Al$_2$ ratio determined by $^{29}$Si-NMR after calcination is the ratio of silicon to aluminum that are retained in the zeolite framework even after calcination. Since aluminum elimination occurs more easily, the $^2$Si-NMR (Si/Al$_2$ ratio)/XRF (Si/Al$_2$ ratio) in terms of % tends to be 100% or higher. In particular, in the case of a CON zeolite in which Al is introduced into the framework in two stages by a post-treatment after hydrothermal synthesis, the amount of aluminum of the bulk increases, however uptake into the framework itself is limited, and Al is present outside the framework in a large amount.

On the other hand, since a CON zeolite of the present embodiment has good crystallinity despite a low Si/Al$_2$ ratio, elimination of Al is not apt to occur even by calcination. This is a characteristic that leads to high durability in use, which is a favorable characteristic when the zeolite is used as a catalyst. Specifically, the ratio of the Si/Al$_2$ ratio of a zeolite after calcination obtained by $^{29}$Si-NMR to the Si/Al$_2$ ratio of the bulk, which may be expressed by [$^{29}$Si-NMR (Si/Al$_2$ ratio)/elemental analysis (Si/Al$_2$ ratio)], is in terms of % preferably 80% or more, more preferably 90% or more, and further preferably 100% or more; and is preferably 200% or less, more preferably 180% or less, further preferably 160 mass % or less, and especially preferably 140 mass % or less.

($^{27}$Al-NMR)

In general, aluminum (Al) in a zeolite crystal is mostly a tetracoordinated Aluminum (hereinafter referred to as "tetracoordinated Al") incorporated into the framework, or a hexacoordinated aluminum (hereinafter referred to as "hexacoordinated Al") existing outside the framework. When the amount of the tetracoordinated Al is large, the number of Bronsted acid sites is also large. For this reason, it is preferable that a CON zeolite of the present embodiment contains more tetracoordinated Al. In a CON zeolite of the present embodiment, the percentage of tetracoordinated Al with respect to the total of tetracoordinated Al and hexacoordinated Al (hereinafter referred to as "tetracoordinated Al rate") is usually 70% or more, preferably 80% or more, more preferably 90% or more, and further preferably 95% or more. Since the tetracoordinated Al rate is the percentage of tetracoordinated Al in aluminum in the crystal, its value is 100% or less. The tetracoordinated Al rate is a value obtained from the following formula.

Tetracoordinated Al rate (%)=[Tetracoordinated Al/
(Tetracoordinated Al+Hexacoordinated Al)]×100

In the above formula, Tetracoordinated Al is the area of the peak having the peak top at 55±5 ppm in $^{27}$Al-NMR and Hexacoordinated Al is the area of the peak having the peak top at 0±5 ppm in $^{27}$Al-NMR.

2. Method of Producing CON Zeolite

A method of producing a CON zeolite of the present embodiment comprises hydrothermal synthesis using a mixture which contains a silicon source, an aluminum source, an alkali metal source and/or an alkaline earth metal source, an organic structure-directing agent and water, and produces the CON zeolite which has the molar ratio of aluminum to silicon higher than 0.01, and which is coded as CON according to the specifications of the International Zeolite Association (IZA). It is preferable to produce a zeolite having a crystal of polymorph B.

A CON zeolite of the present embodiment may be produced by common procedures for hydrothermal synthesis of zeolite except for the above characteristics. Namely, the zeolite may be synthesized by a method in which a crystal precursor mixture including a silicon source, an aluminum source, an alkali metal element source and/or an alkaline earth metal element source, an organic structure-directing agent, water, and if necessary, a seed crystal is prepared, and subjected to hydrothermal synthesis.

An example of a production method will be described below.

(Components of Mixture)

(a) Silicon Source

There is no particular restriction on the silicon source used in the present embodiment, and examples thereof include a silicate, such as fine powdered silica, silica sol, silica gel, silicon dioxide, and water glass, an alkoxide of silicon, such as tetramethoxysilane and tetraethoxysilane, and a halide of silicon. Further, a silica-containing zeolite, such as FAU zeolite, and CHA zeolite, and silicoaluminophosphate may be used as a silicon source.

These silicon sources may be used singly, or in a combination of two or more kinds thereof.

Among these silicon sources, fine powdered silica, silica sol, water glass, silica-containing zeolite, and the like are preferably used from the viewpoint of cost advantages and ease of handling, and more preferably silica sol, water glass, and silica-containing zeolite are used from the viewpoint of reactivity.

(b) Aluminum Source

There is no particular restriction on the aluminum source used in the present embodiment, and examples thereof include amorphous aluminum hydroxide, aluminum hydroxide having a gibbsite structure, aluminum hydroxide having a bayerite structure, aluminum nitrate, aluminum sulfate, aluminum oxide, sodium aluminate, boehmite, pseudoboehmite, alumina sol, and an aluminum alkoxide. Further, an aluminum-containing zeolite, such as FAU zeolite, and CHA zeolite, or aluminophosphate may be used as an aluminum source.

These aluminum sources may be used singly, or in a combination of two or more kinds thereof.

Among these aluminum sources, amorphous aluminum hydroxide, aluminum hydroxide having a gibbsite structure, aluminum hydroxide having a bayerite structure, and an aluminum-containing zeolite are used preferably from the viewpoint of cost advantages and ease of handling, and amorphous aluminum hydroxide, and an aluminum-containing zeolite are used more preferably from the viewpoint of reactivity.

(c) Alkali Metal Element Source and/or Alkaline Earth Metal Element Source

There is no particular restriction on an alkali metal element and an alkaline earth metal element included in the mixture to be subjected to hydrothermal synthesis according to the present embodiment, and examples thereof include lithium, sodium, potassium, rubidium, cesium, beryllium, magnesium, calcium, strontium, and barium. Although these may be included singly, or two or more of them may be included, it is preferable that an alkali metal element is included in view of high alkalinity, and easy crystallization of zeolite especially when a soluble raw material is used.

Examples of an alkali metal element source, and an alkaline earth metal element source include a hydroxide, a chloride, a bromide, an iodide, a hydrogencarbonate, and a carbonate thereof. Among these compounds, the hydroxide, the hydrogencarbonate, and the carbonate are basic in an aqueous solution state. Specific examples thereof include a hydroxide, such as lithium hydroxide, sodium hydroxide, potassium hydroxide, cesium hydroxide, calcium hydroxide, strontium hydroxide, and barium hydroxide; a hydrogencarbonate, such as lithium hydrogencarbonate, sodium hydrogencarbonate, potassium hydrogencarbonate, cesium hydrogencarbonate, calcium hydrogencarbonate, strontium hydrogencarbonate, and barium hydrogencarbonate; a carbonate, such as lithium carbonate, sodium carbonate, potassium carbonate, cesium carbonate, calcium carbonate, strontium carbonate, and barium carbonate. Among them, a hydroxide of an alkali metal, such as lithium hydroxide, sodium hydroxide, potassium hydroxide, and cesium hydroxide, is preferable from the viewpoint of high alkalinity and a promoting effect on dissolution of a raw material and subsequent crystallization of zeolite; sodium hydroxide, potassium hydroxide, and cesium hydroxide are more preferable; and sodium hydroxide, and potassium hydroxide are further preferable.

These alkali metal sources and alkaline earth metal sources may be used singly, or in a combination of two or more kinds thereof.

(d) Organic structure-directing agent

As an organic structure-directing agent (also called as "template"; an organic structure-directing agent is hereinafter occasionally referred to as "SDA"), a publicly known substance, such as tetraethylammonium cation (TEA), and tetrapropylammonium cation (TPA) may be used. Also, as a nitrogen-containing organic structure-directing agent, for example described in U.S. Pat. No. 5,512,267, N,N,N-trimethyl-(−)-cis-myrtanylammonium cation may be used. In addition, it may contain N,N,N-trimethyl-(+)-cis-myrtanylammonium cation, hexamethonium cation, pentaethonium cation, trimethylbenzylammonium cation, and the like.

Further, as a phosphorus-containing organic structure-directing agent, various known substances, such as tetraethylphosphonium, tetrapropylphosphonium, tetrabutylphosphonium, and diphenyldimethylphosphonium, may be used.

However, since a phosphorus compound may generate harmful diphosphorus pentoxide in calcination of the synthesized zeolite to remove SDA, it is preferable to use a nitrogen-containing organic structure-directing agent.

The above ammonium cation, or phosphonium cation accompanies an anion, which does not inhibit formation of a CON zeolite of the present embodiment. Although there is no particular restriction on the anion, specific examples thereof include a halogen ion, such as $Cl^{-1}$, $Br^{-1}$, and $I^{-1}$, a hydroxide ion, an acetate, a sulfate, and a carboxylate. Among these, a hydroxide ion is used especially preferably.

The organic structure-directing agents may be used singly, or in a combination of two or more kinds thereof.

(e) Water

Usually, ion exchanged water is used.

(f) Seed Crystal

A seed crystal may be added to the mixture to be subjected to hydrothermal synthesis according to the present embodiment. As the seed crystal, a zeolite containing in the framework one of bea, bre, lau, and mel, which are defined as composite building units by the International Zeolite Association (IZA), is preferable. Specific examples thereof include *BEA type, CON type, IFR type, MSE type, STT type, BOG type, BRE type, HEU type, IWR type, IWW type, RRO type, STI type, TER type, ASV type, ATO type, BCT type, DFO type, EZT type, ITH type, LAU type, MSO type, OSI type, —RON type, SAO type, TUN type, UOZ type, DON type, MEL type, MFI type, MWW type, and SFG type; and *BEA type, CON type, IER type, MSE type, and STT type are more preferable; *BEA type, CON type, and MSE type are further preferable; and CON type is especially preferable.

Examples of the CON zeolite include, but not limited to, B—CON containing boron, Al—CON including aluminum, B,Al—CON containing boron and aluminum, B,Fe—CON containing boron and iron, B,Ga—CON containing boron and gallium, Ge—CON containing germanium, Ge,B—CON containing germanium and boron, and Ge,Al—CON containing germanium and aluminum. Preferable are B—CON, B,Al—CON, and Al—CON; more preferable are B—CON, and B,Al—CON; and further preferable is B,Al—CON. Use of a CON zeolite containing boron and/or aluminum in the framework is preferable, because crystallization occurs efficiently.

Only one kind of seed crystal may be used, or a combination of those having different structures or compositions may be also used. There is no particular restriction on the composition of a zeolite used as a seed crystal, insofar as it does not greatly affect the composition of the mixture.

Although there is no particular restriction on the particle diameter of a zeolite to be used as a seed crystal, it is usually 0.03 μm or more as an average primary particle diameter, preferably 0.05 μm or more, more preferably 0.1 μm or more, and further preferably 0.2 μm or more; and usually 5 μm or less, preferably 2 μm or less, more preferably 1 μm or less, and further preferably 0.60 μm or less. By adjusting the average primary particle diameter of a seed crystal within the above range, the solubility of the seed crystal in the mixture is increased, formation of a by-product is suppressed, and crystallization of a CON type phase may be promoted efficiently.

As a seed crystal, either of a zeolite containing a structure-directing agent having not undergone calcination after hydrothermal synthesis, and a calcined zeolite not containing a structure-directing agent may be used. For the sake of effective functioning as a crystal nucleus, it is preferable to use a zeolite containing structure-directing agent, because a seed crystal should preferably not dissolve too much at the initial stage of crystallization. However, the solubility of a zeolite containing a structure-directing agent may not be sufficient under a condition of low alkali concentration, a condition of low synthesis temperature, or the like. In such a case, it is preferable to use a zeolite that does not contain a structure-directing agent.

A seed crystal may be added to the mixture in a form of a dispersion in a suitable solvent such as water, or added as it is without being dispersed.

(g) The Other Element M Source

A CON zeolite in the present embodiment may contain at least one element M selected out of boron, gallium, and iron (hereinafter simply referred to as "element M"), in addition to silicon, oxygen, aluminum, alkali metal elements, and alkaline earth metal elements as constituent elements.

The mixture used in hydrothermal synthesis may contain an element M source. There is no particular restriction on the element M source, and it may be selected from, for example, a sulfate, a nitrate, a hydroxide, an oxide, an alkoxide of the elements, and an element M-containing zeolite.

Among the element M sources, from the viewpoint of reactivity, a sulfate, a nitrate, a hydroxide, and an alkoxide are preferable, and from the viewpoint of cost and workability a sulfate, a nitrate, and a hydroxide are more preferable.

As a boron source, boric acid, sodium borate, boron oxide, a boron-containing zeolite, etc. are usually used; preferable are boric acid and sodium borate; and more preferable is boric acid.

As a gallium source, gallium sulfate, gallium nitrate, gallium oxide, gallium chloride, gallium phosphate, gallium hydroxide, a gallium-containing zeolite, etc. are usually used; preferable are gallium sulfate and gallium nitrate; and more preferable is gallium sulfate.

As an iron source, iron nitrate, iron sulfate, iron oxide, iron chloride, iron hydroxide, an iron-containing zeolite, etc. are usually used; preferable are iron sulfate and iron nitrate; and more preferable is iron sulfate.

The element M sources may be used singly, a combination of two or more of the same element may be used, or one with different elements, or a combination of two or more with different elements may be used.

Also, the mixture may contain a source of another metal (lead, germanium, titanium, zirconium, tin, chromium, cobalt, etc.). The sources may be contained singly, or two or more may be included in the mixture.

(Composition of Mixture)

A preferred composition of the mixture (slurry or gel) to be subjected to hydrothermal synthesis in the present embodiment is as follows.

In a case in which a seed crystal is added, the following compositions are values calculated excluding silicon, aluminum, an element M, an alkali metal element, an alkaline earth metal, a structure-directing agent, and water (adsorbed water) contained in a seed crystal.

Although there is no particular restriction on the molar ratio (Al/Si) of the aluminum atom to the silicon atom in the mixture, it is usually more than 0.01, preferably 0.015 or more, more preferably 0.02 or more, further preferably 0.04 or more, especially preferably 0.06 or more, and most preferably 0.08 or more; and is usually 0.30 or less, preferably 0.20 or less, more preferably 0.15 or less, further preferably 0.12 or less, and especially preferably 0.10 or less. When the molar ratio of aluminum atom to silicon atom is within the above range, the CON type is prone to be formed, and the synthesis yield is improved. Further, when the product is used as a catalyst, an organic compound material may be efficiently converted by an acid site derived from Al, which is preferable.

Although there is no particular restriction on the molar ratio of the sum of an alkali metal atom and an alkaline earth metal atom to the silicon atom [(alkali metal atom+alkaline earth metal atom)/Si] in the mixture metal, it is usually 0 or more, preferably 0.10 or more, more preferably 0.20 or more, further preferably 0.25 or more, and especially preferably 0.30 or more; and is usually 0.60 or less, preferably 0.50 or less, more preferably 0.45 or less, further preferably 0.40 or less, and especially preferably 0.35 or less. By adjusting the ratio within the above range, incorporation of aluminum into the CON zeolite framework becomes sufficient, and the synthesis yield is improved. Also, formation of a by-product may be suppressed, and the crystallization rate to the CON phase may be favorably accelerated.

Although there is no particular restriction on the molar ratio of the sum of the alkali metal atom and the alkaline earth metal atom to the aluminum atom [(alkali metal atom+alkaline earth metal atom)/Al] in the mixture, it is usually 1 or more, preferably 2 or more, more preferably 3 or more, and further preferably 4 or more; and is usually 20 or less, preferably 15 or less, more preferably 10 or less, and further preferably 7 or less. By adjusting the ratio within the above range, interaction between the alkali metal and alkaline earth metal, and aluminum during crystallization becomes effective, so that CON zeolite is likely to be obtained, which is preferable.

Although there is no particular restriction on the content of an organic structure-directing agent in the mixture, the molar ratio of a structure-directing agent to the silicon atom (organic structure-directing agent/Si) is usually 0.01 or more, preferably 0.02 or more, more preferably 0.05 or more, further preferably 0.10 or more, and especially preferably 0.15 or more; and is usually 0.60 or less, preferably 0.50 or less, more preferably 0.40 or less, further preferably 0.30 or less, and especially preferably 0.25 or less. By adjusting an organic structure-directing agent in the mixture within the above range, nucleation in the mixture is promoted, so that crystallization of a CON zeolite is promoted, and synthesis in high yield may be achieved, which is preferable. In addition, the amount of an expensive organic structure-directing agent to be used may be suppressed, and the production cost of zeolite may be reduced, which is also preferable.

Although there is no particular restriction on the molar ratio of the sum of the organic structure-directing agent, the alkali metal atom, and the alkaline earth metal atom to the aluminum atom [(organic structure-directing agent+alkali metal atom+alkaline earth metal atom)/Al] in the mixture metal, it is usually 1 or more, preferably 3 or more, more preferably 5 or more, and further preferably 6 or more; and is usually 50 or less, preferably 30 or less, more preferably 20 or less, and further preferably 10 or less. By adjusting the ratio within the above range, interaction between aluminum and an organic structure-directing agent, an alkali metal, and an alkaline earth metal during crystallization becomes effective, so that a CON zeolite is easily obtained, which is preferable.

It is preferable that N,N,N-trimethyl-(−)-cis-myrtanylammonium cation is included in the organic structure-directing agent in the mixture. Although there is no particular restriction on the molar ratio of N,N,N-trimethyl-(−)-cis-myrtanylammonium cation (hereinafter referred to as "TMMA") to the total organic structure-directing agents [TMMA/organic structure-directing agents (TMMA+others)], it is usually 0 or more, preferably 0.20 or more, more preferably 0.40 or more, further preferably 0.60 or more, especially preferably 0.80 or more, and the upper limit is 1.0. The higher ratio of TMMA is preferable because crystallization of the CON framework proceeds easily.

Although there is no particular restriction on the content of water in the mixture, the molar ratio of $H_2O$ to silicon ($H_2O$/Si) is usually 5 or more, preferably 7 or more, more preferably 9 or more, and further preferably 10 or more; and is usually 50 or less, preferably 40 or less, more preferably 30 or less, and further preferably 25 or less. By adjusting the content of water in the mixture within the above range, crystallization may be promoted. In addition, the productivity per reactor may be increased. Further it is advantageous because deterioration of the mixing property by stirring due to increase in viscosity during the reaction may be suppressed, and the waste liquid treatment cost may be curtailed.

Although there is no particular restriction on the amount of a seed crystal added to the mixture, its content with respect to $SiO_2$, wherein silicon (Si) included in the mixture other than the seed crystal is assumed to be totally $SiO_2$, is usually 0.1 mass % or more, preferably 1 mass % or more, more preferably 2 mass % or more, and further preferably 4 mass % or more; and the upper limit is usually 20 mass % or less, preferably 15 mass % or less, more preferably 10 mass % or less, and further preferably 8 mass %, or less, provided that there is no particular restriction thereon. By adjusting the amount of a seed crystal within the above range, the amount of the precursor directed to the CON framework becomes sufficient and crystallization may be promoted. Further, since the amount of components derived from the seed crystal to be contained in the product is suppressed, and the productivity may be enhanced, the production cost may be reduced.

(Preparation of Reactant Mixture)

In the production method according to the present embodiment, a reactant mixture prepared by mixing the aforedescribed silicon source, aluminum source, alkali metal source, and/or alkaline earth metal source, organic structure-directing agent, and water is subjected to hydrothermal synthesis. Although there is no particular restriction on the mixing order of these raw materials, it is preferable that firstly water, an alkali metal element source and/or an alkaline earth metal element source, and an organic structure-directing agent are mixed to prepare an alkaline solution, and then an aluminum source, a silicon source, and, if necessary, a seed crystals are mixed in this order, because the raw materials may be dissolved more uniformly if a silicon source, and an aluminum source are added after the alkaline solution is prepared.

(Maturing)

The reactant mixture prepared as described above may be subjected to hydrothermal synthesis immediately after its preparation, but the same may be matured for a certain period of time under a predetermined temperature condition in order to obtain a zeolite having high crystallinity. Especially in scaling-up, the stirring property is likely to deteriorate and the mixed state of raw materials tends to be insufficient. Therefore, it is preferable to improve the reaction mixture into a more uniform state by means of maturing with stirring for a certain period of time. The maturing temperature is usually 100° C. or less, preferably 95° C. or less, and more preferably 90° C. or less; and is usually 0° C. or more, and preferably 10° C. or more, although the lower limit thereof is not particularly provided. The maturing temperature may be constant throughout the maturing, or it may be changed stepwise or continuously. Although there is no particular restriction on the maturing time, it is usually 2 hours or more, preferably 3 hours or more, and more preferably 5 hours or more; and is usually 14 days or less, preferably 7 days or less, and more preferably 3 days or less.

(Hydrothermal Synthesis Step)

A CON zeolite may be produced by heating the mixture in a reactor (hydrothermal synthesis).

There is no particular restriction on the heating temperature (reaction temperature), and it is usually 120° C. or more, preferably 140° C. or more, more preferably 160° C. or more, and further preferably 170° C. or more; and is usually 220° C. or less, preferably 200° C. or less, more preferably 190° C. or less, and further preferably 185° C. or less. By adjusting the reaction temperature within the above range, the crystallization time of a CON zeolite may be shortened, and the yield of zeolite is improved. In addition, it is preferable because by-production of a zeolite having a different structure may be suppressed. The reaction temperature may be constant throughout the reaction, or it may be changed stepwise or continuously.

There is no particular restriction on the time required for raising the temperature to the heating temperature (reaction temperature), and it is usually 0.1 hour or more, preferably 0.5 hours or more, and more preferably 1 hour or more, and there is no particular upper limit of the time required for raising the temperature.

The heating time (reaction time) is usually 1 hour or more, preferably 5 hours or more, and more preferably 10 hours or more; and the upper limit is usually 30 days or less, preferably 10 days or less, more preferably 7 days or less, and further preferably 5 days or less. By adjusting the reaction time within the above range, the yield of a CON zeolite may be improved, and by-production of a zeolite having a different structure may be suppressed, which is preferable.

There is no particular restriction on the pressure at the time of the reaction, and an autogenous pressure generated when a hermetically closed container filled with the mixture is heated to the above temperature range suffices. If necessary, an inert gas such as nitrogen may be added.

(Collection of CON Zeolite)

After the hydrothermal synthesis, the product CON zeolite is separated from the hydrothermal synthesis reaction solution.

The obtained zeolite (hereinafter referred to as "zeolite containing SDA, etc.") contains either or both of an organic structure-directing agent and an alkali metal in the pores. There is no particular restriction on a method for separating a zeolite containing SDA, etc. from the hydrothermal synthesis reaction solution, and examples thereof usually include a method, such as filtration, decantation, and direct drying.

A zeolite containing SDA, etc. separated and collected from the hydrothermal synthesis reaction solution is, for removing an organic structure-directing agent, etc. used during production, washed with water and dried according to need and thereafter subjected to calcination, etc. to yield a zeolite not containing an organic structure-directing agent. From the viewpoint of production efficiency, removal by calcination is desirable.

When a CON zeolite of the present embodiment is used for an application of a catalyst (including a catalyst carrier), an adsorbent, and the like, it is used, if necessary, after removing them, The calcination temperature is usually 350° C. or higher, preferably 400° C. or higher, and more preferably 450° C. or higher; and the upper limit is usually 900° C. or lower, preferably 850° C. or lower, and more preferably 800° C. or lower. By adjusting the calcination temperature within the above range, a structure-directing agent may be efficiently removed, and the pore volume of the zeolite becomes sufficiently large. Further, collapse of zeolite framework and decrease in crystallinity may be suppressed.

There is no particular restriction on the calcination time, insofar as a structure-directing agent is sufficiently removed. It is preferably 1 hour or more, and more preferably 3 hours or more; and the upper limit is usually 24 hours or less.

The calcination is preferably carried out in an atmosphere containing oxygen, and is usually carried out in an air atmosphere.

Although there is no particular restriction on the application of a CON zeolite of the present embodiment, it is favorably used as a catalyst, an adsorbent, a separation material, or the like. In particular, it is favorably used as a hydrocarbon adsorbent, a catalyst for purifying an exhaust gas of an automobile, etc. In particular, a CON zeolite having an Al/Si ratio of 0.04 or more may obtain high adsorption performance and catalytic activity.

3. Method of Producing Lower Olefin and Aromatic Hydrocarbon

The present embodiment has also an aspect as a method of producing a lower olefin and an aromatic hydrocarbon from an organic compound raw material. That is, it may be favorably used for producing lower olefins by interconversion of lower olefins such as ethylene and propylene, and for producing an aromatic hydrocarbon by a dehydrocyclization reaction. It may also be favorably used for producing a lower olefin (MTO: methanol to olefin) and for producing an aromatic hydrocarbon (methanol to aromatics) by conversion of a raw material containing an oxygenate, such as methanol and dimethyl ether.

(Ethylene)

There is no particular restriction on ethylene, which is a raw material according to the present embodiment. For example, ethylene produced by catalytic cracking or steam cracking from a petroleum source, ethylene obtained by performing Fischer-Tropsch synthesis using as a raw material a hydrogen/CO mixed gas obtained by gasification of coal, ethylene obtained by dehydrogenation or hydrogenation of ethane, ethylene obtained by a metathesis reaction and a homologation reaction, ethylene obtained by a MTO (methanol to olefin) reaction, ethylene obtained by a dehydration reaction of ethanol, ethylene obtained by oxidative coupling of methane, or ethylene obtained by any of various known methods may be used optionally. In this case, a mixture containing optionally another compound derived from various production methods in addition to ethylene may be used as it is, however purified ethylene is preferable. In addition, since ethanol is immediately converted to ethylene by dehydration, ethanol may be used as it is as a raw material.

(Methanol, and Dimethyl Ether)

There is no particular restriction on the production origin of methanol and dimethyl ether, which are raw materials according to the present embodiment. Examples of thereof include a product obtained by a hydrogenation reaction of a mixed gas of CO/hydrogen derived from a by-product in steel industry, coal, and natural gas; a product obtained by a reforming reaction of alcohols of vegetable-origin; a product obtained by a fermentation method; and a product obtained from organic materials, such as recycled plastics and municipal waste. In this case, a mixture containing another compound derived from each production methods in addition to methanol and dimethyl ether may be used as it is, however purified mixture may be also used.

As a reaction raw material, only methanol may be used, only dimethyl ether may be used, or a mixture thereof may be used. When methanol and dimethyl ether are used as a mixture, there is no particular restriction on the mixing ratio.

As a reaction raw material, at least one selected from methanol and dimethyl ether may be mixed with ethylene. When these are mixed and used, there is no particular restriction on the mixing ratio.

(Reactor)

There is no particular restriction on the reaction mode in the present embodiment, insofar as an organic compound raw material is in a gas phase in the reaction zone, and a fixed bed reactor, a moving bed reactor, and a fluidized bed reactor may be selected. In this connection, although any form out of a batch, a semi-continuous, or a continuous type may be carried out, a continuous type is preferable, and in such a case, either of a method using a single reactor, or a method using a plurality of reactors arranged in series or in parallel may be conducted.

When a fluidized bed reactor is filled with the catalyst, a granular material inert to the reaction, such as quartz sand, alumina, silica, and silica-alumina may be mixed with the catalyst for filling in order to control the temperature distribution of the catalyst layer to be narrow. In this case, there is no particular restriction on the usage amount of the granular material inert to the reaction, such as quartz sand. In this regard, it is preferable that the granular material has a particle diameter similar to the catalyst from the viewpoint of uniform mixing with the catalyst.

A reaction substrate (reaction raw material) may be fed to the reactor divisionally for the sake of dispersing heat to be generated by the reaction.

(Substrate Concentration)

Although there is no particular restriction on the total concentration of organic compound raw materials (substrate concentration) in all the supply components to be supplied to the reactor, it is usually 5 mol % or more of the total supply, preferably 10 mol % or more, more preferably 20 mol % or more, further preferably 30 mol % or more, and especially preferably 50 mol % or more; and is usually 95 mol % or less, preferably 90 mol % or less, and more preferably 70 mol % or less. By adjusting the substrate concentration within the above range, formation of a heavy hydrocarbon component and a paraffin may be suppressed, and the yield of a lower olefin and an aromatic hydrocarbon may be improved. Further, since the reaction rate may be maintained, the amount of catalyst may be suppressed and the size of the reactor may be suppressed.

Therefore, it is preferable to dilute the reaction substrate with a diluent described below according to need so as to realize such a preferable substrate concentration.

(Diluent)

In the reactor, in addition to the organic compound raw materials, a gas inert to the reaction including helium, argon, nitrogen, carbon monoxide, carbon dioxide, hydrogen, water, paraffins, hydrocarbons such as methane, aromatic compounds, and mixtures thereof may be present; and coexistence of helium, nitrogen, and water (steam) is favorable, because separation is easy.

As such a diluent, impurities contained in the reaction raw materials may be used as they are, or a diluent prepared separately may be mixed with the reaction raw materials and used.

Further, the diluent may be mixed with the reaction raw material before entering the reactor, or may be supplied to the reactor separately from the reaction raw material.

(Weight Space Velocity)

The weight space velocity referred to herein is the flow rate of an organic compound as the reaction raw material per weight of the catalyst (catalytically active component), wherein the weight of the catalyst means the weight of a catalytically active component excluding an inactive component and a binder to be used for granulation or forming of the catalyst.

Further, the flow rate means the total flow rate (weight/hour) of the organic compound raw materials (ethylene, and/or methanol, and/or dimethyl ether, etc.).

Although there is no particular restriction on the weight space velocity, it is usually 0.01 $Hr^{-1}$ or more, preferably 0.1 $Hr^{-1}$ or more, more preferably 0.3 $Hr^{-1}$ or more, and further preferably 0.5 $Hr^{-1}$; and is usually 50 $Hr^{-1}$ or less, preferably 20 $Hr^{-1}$ or less, more preferably 10 $Hr^{-1}$ or less, and further preferably 5.0 $Hr^{-1}$ or less. By adjusting the weight space velocity within the above range, the proportion of an unreacted organic compound raw material in the reactor outlet gas may be reduced, and the amount of by-products such as heavy hydrocarbon components and paraffins may be reduced, so that the yield of a lower olefin and an aromatic hydrocarbon may be improved. In addition, by doing so, the amount of catalyst necessary for obtaining a certain production amount may be reduced, which is preferable for suppressing the size of the reactor.

(Reaction Temperature)

There is no particular restriction on the reaction temperature, insofar as it is a temperature at which a lower olefin and an aromatic hydrocarbon is formed when an organic compound raw material gets in contact with a catalyst. It is usually 250° C. or higher, preferably 300° C. or higher, more preferably 350° C. or higher, and further preferably 400° C. or higher; and is usually 650° C. or lower, preferably 600° C. or lower, more preferably 550° C. or lower, and further preferably 500° C. or lower. By adjusting the reaction temperature within the above range, the productivity may be increased while suppressing coking. Further, since aluminum elimination from the zeolite framework is suppressed, the catalyst life may be maintained, which is preferable. In this regard, the reaction temperature means herein the temperature at the outlet of the catalyst layer.

(Reaction Pressure)

Although there is no particular restriction on the reaction pressure, it is usually 0.01 MPa or more (absolute pressure, the same applies hereinbelow), preferably 0.05 MPa or more, more preferably 0.1 MPa or more, and further preferably 0.2 MPa or more; and is usually 5 MPa or less, preferably 1 MPa or less, more preferably 0.7 MPa or less, and further preferably 0.5 MPa or less. When the reaction pressure is within the above range, the yield of a lower olefin and an aromatic hydrocarbon may be improved.

(Raw Material Partial Pressure)

Although there is no particular restriction on the total partial pressure of organic compound raw materials, it is usually 0.005 MPa or more (absolute pressure, the same applies hereinbelow), preferably 0.01 MPa or more, further preferably 0.03 MPa or more, further preferably 0.05 MPa or more, and especially preferably 0.07 MPa or more; and is usually 3 MPa or less, preferably 1 MPa or less, more preferably 0.5 MPa or less, further preferably 0.3 MPa or less, and especially preferably 0.1 MPa or less. By adjusting the partial pressures of a raw materials within the above range, coking may be suppressed and the yield of a lower olefin and an aromatic hydrocarbon may be improved. The reaction rate may also be maintained.

(Conversion)

Although there is no particular restriction on the conversion of methanol and/or dimethyl ether in the present embodiment, the conversion is usually 90% or more, preferably 95% or more, more preferably 99% or more, and further preferably 99.5% or more; and is usually 100% or less. Meanwhile, although the conversion of ethylene is not particularly limited, the conversion is usually 50% or more, preferably 60% or more, and more preferably 70% or more; and is usually less than 100%, preferably 95% or less, and more preferably 90% or less.

Usually with the reaction time, accumulation of coke proceeds, and the conversion of an organic compound raw material tends to decrease. Therefore, the catalyst used for the reaction for a certain period of time needs to be subjected to a regeneration treatment. There is no particular limitation on a method of operation in the above conversion range.

For example, when a reaction is carried out in a fixed bed reactor, a plurality of reactors are provided in parallel, and when the conversion falls below the above preferable range, the contact between the catalyst and the reaction raw material is stopped and the catalyst is subjected to a regeneration step. In a fixed bed reactor, the reaction time and the regeneration time are adjusted appropriately, in other words, the switching timing from a reaction step to a regeneration step during operation is regulated appropriately so that the operation may be carried out continuously at a conversion in the above preferred range.

In a case in which the reaction is conducted in a fluidized bed reactor, it is preferable to attach a catalyst regenerator to the reactor and to perform the reaction while transferring continuously the catalyst discharged from the reactor to the regenerator, and returning continuously the catalyst regenerated in the regenerator to the reactor. By adjusting appropriately the residence time of the catalyst in the reactor and the residence time in the regenerator, it is possible to perform the operation continuously at a conversion in the above preferred range.

A catalyst which conversion of an organic compound raw material has been declined may be regenerated utilizing various known catalyst regenerating methods.

Although there is no particular restriction on the regeneration method, specifically it may be regenerated using, for example, air, nitrogen, steam, or hydrogen, and regeneration using air or hydrogen is preferable.

(Reaction Product)

As the reactor outlet gas (reactor effluent), a mixed gas containing a lower olefin, such as ethylene, propylene, and butene, an aromatic hydrocarbon, such as benzene, toluene, and xylene, as reaction products, as well as a by-product and a diluent is obtained. Although there is no particular restriction on the concentration of the target components in the mixed gas, it is usually 5 mass % or more, and preferably 10 mass % or more; and is usually 95 mass % or less, and preferably 90 mass % or less.

Depending on the reaction conditions, an unreacted raw material may be included in the reaction product, it is preferable to carry out the reaction under such reaction conditions that the amount of the unreacted raw material becomes minimal. By doing so, separation of the reaction product from the unreacted raw material becomes easy, and preferably unnecessary.

(Separation of Product)

The mixed gas as the reactor outlet gas containing a lower olefin and an aromatic hydrocarbon as the reaction products, an unreacted raw material, a by-product and a diluent, may be introduced into a known separation and purification facility, and subjected to treatments for collection, purification, recycling, and discharging corresponding to each component.

4. Adsorbent

Another aspect of the present invention also has an aspect as an adsorbent for an inorganic gas or a hydrocarbon component. Specifically, it relates to a use as an adsorbent for a hydrocarbon gas, especially for an exhaust gas as formed during combustion of a hydrocarbon, and more specifically it relates to adsorption of a hydrocarbon gas formed in a cold start operation of an internal combustion engine.

Prospective low emission standards for vehicles force automobile manufacturers and catalyst manufacturers to focus on reduction of hydrocarbon emissions during a cold start. This is because a large portion of the hydrocarbon emissions occur during the cold start period. Therefore, it is essential to control the emissions during a cold start operation of a vehicle equipped with an internal combustion engine. A fresh catalyst begins to function at a relatively low temperature around 170° C., but in the case of a catalysts used for many years the minimum functioning temperature rises and the catalyst begins to function at about 200° C. to 220° C. Such a catalyst usually requires at least 1 to 2 min to reach such temperatures, and approximately 70% of the hydrocarbon emission occurs in the low temperature range. In other words, at lower temperatures, where the catalyst in the catalytic converter is not able to convert effectively an incompletely combusted hydrocarbon to the final combustion products, it is desired that a hydrocarbon adsorbent adsorbs to trap the hydrocarbons discharged from an engine (hydrocarbon trap, HC trap) before they reach the catalytic converter. The desorption temperature is preferably equal to or higher than the activation temperature of the catalyst.

An important requirement for a hydrocarbon trapping material is the adsorption ability of the adsorbent, that is, the desorption temperature at which an adsorbed hydrocarbon is desorbed and sent to a catalytic converter, and the hydrothermal stability of the adsorbent.

Various zeolites having a BEA framework have been heretofore investigated as a hydrocarbon trapping material. However, it has been found that a BEA zeolite has insufficient hydrothermal stability, and the decline of the adsorption ability advances over a prolonged use. Therefore, there is a demand for a hydrocarbon trapping material capable of adsorbing and trapping a hydrocarbon component discharged during a cold start of an internal combustion engine (period until the catalyst is activated).

A CON zeolite of the present embodiment has a high adsorption ability and a high hydrothermal stability that can withstand a limited space due to an automobile on-board use, and a wide range of exhaust gas environment associated with engine operating conditions. Therefore, it may be favorably used as a hydrocarbon trapping material.

For an application as a hydrocarbon trapping material, a CON zeolite of the present embodiment may be used singly, or in a mixture with other zeolites.

Further, an adsorbent containing a CON zeolite of the present embodiment may be mixed and formed with a binder, such as silica, alumina, and a clay mineral. Examples of the clay mineral include kaolin, sepiolite, montmorillonite, bentonite, attapulgite, and talc. It may be applied to a substrate such as a honeycomb and used. Specifically, for example, a slurry is prepared by mixing a catalyst containing a CON zeolite of the present embodiment, and an inorganic binder, such as silica, alumina, and a clay mineral, and may be applied to the surface of a substrate made of an inorganic material such as cordierite, and used.

The target gas to be adsorbed is, for example, a gas contained in an exhaust gas of an internal combustion engine of a gasoline engine car, a diesel engine car, or the like. Specific examples thereof include an inorganic gas, such as carbon monoxide, carbon dioxide, nitrogen, oxygen, hydrogen, water, sulfur compounds, and nitrogen oxides, and a hydrocarbon gas. Regarding the hydrocarbon gas, a CON zeolite of the present embodiment is effective especially in adsorbing an alkane having a carbon number of approx. 1 to 20, such as methane, ethane, propane, butane, pentane, hexane, n-heptane, and isooctane; an alkene having a carbon number of approx. 2 to 20, such as ethylene, propylene, butene, pentene, methylpentene, hexene, and methylhexene; and aromatics, such as benzene, toluene, xylene, and trimethylbenzene. The zeolite may be used for a single kind of hydrocarbon of the above target gases, or used for a mixture of a plurality of hydrocarbons. When a CON zeolite of the present embodiment is used, the plural kinds of hydrocarbons may be adsorbed at the same time.

Although there is no particular restriction on the contact condition between an adsorbent and an exhaust gas in using an adsorbent containing a CON zeolite of the present embodiment, it is usually 100 $hr^{-1}$ or more, preferably 1,000 $hr^{-1}$ or more, and further preferably 5,000 $hr^{-1}$ or more; and is usually 500,000 $hr^{-1}$ or less, preferably 400,000 $hr^{-1}$ or less, and further preferably 200,000 $hr^{-1}$ or less.

Although there is no particular restriction on the temperature in using an adsorbent containing a CON zeolite of the present embodiment, it is usually 50° C. or more, more preferably 100° C. or more, further preferably 120° C. or more, and especially preferably 150° C. or more; and is usually 800° C. or less, preferably 600° C. or less, more preferably 400° C. or less, and especially preferably 300° C. or less.

5. Exhaust Gas Treatment Catalyst

When a CON zeolite of the present embodiment is used as an exhaust gas treatment catalyst such as a catalyst for purifying an automobile exhaust gas, the CON zeolite of the present embodiment may be used as it is, or a CON zeolite to which a metal is added according to need may be used. Specific examples of a method of adding a metal include a method of impregnation, and a method of ion exchange in a liquid phase or a solid phase. Alternatively, a metal-containing zeolite may be synthesized directly by adding a metal (which may be an elementary substance, or a compound) before the hydrothermal synthesis as described above. As for the presence state of the metal in a metal-containing zeolite, it may be included in the framework, or not included in the framework. Further, it may be used also after being mixed with a binder, such as silica, alumina, and a clay mineral, and granulated or formed. Further, it may be used after being formed into a predetermined shape by a coating method or a forming method, and it may preferably be used after being formed into a honeycomb shape.

When a formed body of a catalyst containing a CON zeolite of the present embodiment is yielded by the coating method, the same may be yielded usually by mixing a CON zeolite of the present embodiment with an inorganic binder, such as silica, and alumina, to prepare a slurry, applying the slurry to the surface of a formed body made of an inorganic material such as cordierite, and performing calcination. By doing so, the slurry is preferably coated on a honeycomb-shaped formed body so as to yield a honeycomb catalyst. Since the above describes an example of an exhaust gas treatment catalyst, an inorganic binder is used, however an organic binder may be also used depending on the application and use conditions.

When a formed body of a catalyst containing a CON zeolite of the present embodiment is yielded by the forming method, the same may be yielded usually by kneading a CON zeolite with an inorganic binder such as silica and alumina, and an inorganic fiber such as an alumina fiber and a glass fiber, forming them by an extrusion method or a compression method, and performing calcination. Preferably, by doing so, a honeycomb catalyst may be yielded by forming into a honeycomb shape.

A catalyst of the present embodiment including a CON zeolite of the present embodiment is effective as a selective reduction catalyst for NOx such as an automobile exhaust gas purification catalyst for removing nitrogen oxides by bringing it into contact with a nitrogen oxide-containing exhaust gas.

An exhaust gas treatment catalyst, in which a metal other than Si and Al is added to a CON zeolite of the present embodiment, is especially effective as a selective reduction catalyst for NOx. With respect to an exhaust gas treatment catalyst, the metal element to be added to the zeolite is preferably a transition metal, and among others the one selected from the group including iron, cobalt, palladium, iridium, platinum, copper, silver, gold, cerium, lanthanum, praseodymium, titanium, and zirconium is preferable. More preferably, it is selected from iron and copper. Two or more of these metals may be added in combination. Cu (copper) is the most preferable. The content of metal elements other than Si and Al with respect to the total amount of CON zeolite to which the metal elements other than Si and Al are added is usually 0.1 weight % or more, preferably 0.3 weight % or more, more preferably 0.5 weight % or more, and especially preferably 1.0 weight % or more; and is usually 20 weight % or less, preferably 10 weight % or less, and more preferably 8 weight % or less.

Especially, when the metal element to be added into the zeolite is copper (Cu), the content thereof in the catalyst is preferably 0.1 weight % or more and 10 weight % or less, and a more preferable range is as described above.

Although there is no particular restriction on the method for adding the metal into a CON zeolite of the present embodiment, a method by which the metal is supported by a CON zeolite, such as an ion exchange method, an impregnation method, a precipitation method, a solid phase ion exchange method, a CVD method, and a spray-drying method, which are commonly used, and more preferable are a solid phase ion exchange method, an impregnation method, and a spray-drying method.

There is no particular restriction on a metal raw material, and usually an inorganic acid salt, such as a sulfate, a nitrate, a phosphate, a chloride, and a bromide; an organic acid salt, such as an acetate, an oxalate, and a citrate; and an organometallic compound, such as a pentacarbonyl and a ferrocene, and the like of the above metals are used. Among the above, from the viewpoint of solubility in water, an inorganic acid salt and an organic acid salt are preferable, and more specifically, for example, a nitrate, a sulfate, an acetate, a hydrochloride, etc. are preferable. In some cases, a colloidal oxide or a fine powder oxide may be used.

As metal raw materials, two or more different kinds of metal species or compound species may be used in combination.

After the metal has been supported on a CON zeolite, it is calcined preferably at 300° C. to 900° C., more preferably at 350° C. to 850° C., and further preferably at 400° C. to 800° C., and for 1 sec to 24 hours, preferably 10 sec to 8 hours, more preferably about 30 min to 4 hours. Although this calcination is not necessarily required, it is effective to conduct calcination for improving the dispersibility of the metal supported in the framework of the zeolite so as to enhance the catalytic activity.

Although there is no particular restriction on the specific surface area of a catalyst yielded in the present embodiment, it is preferably from 300 to 1000 m$^2$/g, more preferably from 350 to 800 m$^2$/g, and further preferably from 450 to 750 m$^2$/g because the number of active sites present on the inner surface of the pores increases. In this regard, the specific surface area of a catalyst is measured by the BET method.

The exhaust gas may include components other than nitrogen oxides and may include, for example, a hydrocarbon, carbon monoxide, carbon dioxide, hydrogen, nitrogen, oxygen, sulfur oxides, and water. When the catalyst is used, a known reducing agent, such as a hydrocarbon, and a nitrogen-containing compound including ammonia, urea, or the like, may be used. Specifically, nitrogen oxides contained in various exhaust gases discharged from various types of diesel engines, boilers, gas turbines, etc. of a diesel engine automobile, a gasoline engine automobile, a stationary power generator, a ship, an agricultural machine, a construction machine, a motorcycle, and an aircraft, may be removed by an exhaust gas treatment catalyst of the present embodiment.

A CON zeolite of the present embodiment may be used in addition to the use as catalysts for removing nitrogen oxides, for example, in a step subsequent to the step where nitrogen oxides are removed using a catalyst for removing nitrogen oxides of the present embodiment, as an oxidation catalyst, which oxidizes an excessive reducing agent (for example, ammonia) not having been consumed in removing nitrogen oxides. In this way a catalyst containing a CON zeolite of the present embodiment is capable of oxidizing an excessive reducing agent as an oxidation catalyst to decrease the reducing agent in an exhaust gas. In that case, a catalyst, in which a metal such as the platinum group is supported on a carrier such as zeolite for adsorbing the reducing agent, may be used as an oxidation catalyst, and a CON zeolite of the present embodiment may be used as the carrier, or as a selective reduction catalyst for nitrogen oxides. For example, a CON zeolite of the present embodiment supporting, for example, iron and/or copper may be used after supporting additionally a metal such as the platinum group.

Although there is no particular restriction on the contact condition of a catalyst with an exhaust gas when a catalyst of the present embodiment is used, the space velocity of the exhaust gas is usually 100 hr$^{-1}$ or more, preferably 1,000 hr$^{-1}$ or more, and more preferably 5,000 hr$^{-1}$ or more; and is usually 500,000 hr$^{-1}$ or less, preferably 400,000 hr$^{-1}$ or less, and more preferably 200,000 hr$^{-1}$ or less. Further, the temperature is usually 100° C. or higher, preferably 125° C. or higher, and more preferably 150° C. or higher; and is usually 1000° C. or lower, preferably 800° C. or lower, more preferably 600° C. or lower, and especially preferably 500° C. or lower.

Another aspect of the present invention will be described in more detail with reference to Example A, but it is not limited to the following Examples unless it departs from the scope and spirit of the present invention.

An X-ray diffraction (XRD) pattern of a crystal of a zeolite obtained by the synthesis in the following Preparation Example A was obtained using an X'Pert PRO MPD produced by Malvern Panalytical B. V. The X-ray source is CuKα (X-ray output: 40 kV, 30 mA), the reading width is 0.016° and the scanning speed is 4.0°/min. In addition, the shape of the particle was observed on a sample having undergone a conductive treatment using a scanning electron microscope (ULTRA 55) produced by Carl Zeiss at an acceleration voltage of 3 kV. The composition of the synthesized zeolite was determined by an ICP elemental analysis based on inductively-coupled plasma atomic emission spectrometry (ICP-AES). For a fluorescent X-ray analysis (XRF), a Rayny EDX-700 produced by Shimadzu Corporation was used.

Preparation Example A

Firstly, 2.57 g of sodium hydroxide (97 mass % or more, produced by Kishida Chemical Co., Ltd.), 288 g of an aqueous solution of N,N,N-trimethyl-(−)-cis-myrtanylammonium hydroxide (hereinafter abbreviated as "TMMAOH") (14.8 mass %, produced by Wako Pure Chemical Industries, Ltd.), 2.47 g of boric acid (produced by Kishida Chemical Co., Ltd.), and 0.407 g of aluminum sulfate (51.0 to 57.5 mass %, produced by Kishida Chemical Co., Ltd.) were mixed, to which 197 g of silica sol SI-30 ($SiO_2$: 30.6 mass %, and $Na_2O$: 0.37 mass %, produced by JGC Catalysts and Chemicals Ltd.) was added as a silica source, and the mixture was stirred sufficiently. Further, 1.20 g of a BEA zeolite ($SiO_2/Al_2O_3$ ratio: 30, HSZ-931 HOA produced by Tosoh Corporation) equivalent to 2 mass % with respect to the added $SiO_2$ was added as a seed crystal and stirring was continued further to obtain a mixture. The mixture was charged in a 1000 mL autoclave, and subjected to a hydrothermal synthesis reaction at 170° C. for 4 days with stirring at 250 rpm under an autogenous pressure. The obtained product was filtrated, washed with water, and dried at 100° C. to obtain 58.9 g of a white powder. From the XRD pattern of the product, it was confirmed that the obtained product was a CON zeolite. From an ICP elemental analysis, the $SiO_2/Al_2O_3$ ratio was 595 and the $SiO_2/B_2O_3$ ratio was 50.

Example A1

Firstly, 0.155 g of sodium hydroxide, 4.16 g of an aqueous solution of N,N,N-trimethyl-(−)-cis-myrtanylammonium hydroxide (30.8 mass %), and 3.65 g of water were mixed, to which 0.960 g of zeolite Y CBV 720 ($SiO_2/Al_2O_3$ ratio: 30, produced by Zeolyst International), and 0.990 g of colloidal silica SI-30 ($SiO_2$: 30 mass %, $Na_2O$: 0.4 mass %, produced by JGC Catalysts and Chemicals Ltd.) were added, and the mixture was stirred for 2 hours. Further, 0.240 g of zeolite CIT-1 ($SiO_2/Al_2O_3$ ratio: 595, $SiO_2/B_2O_3$ ratio: 50) equivalent to 20 mass % with respect to the added $SiO_2$ was added as a seed crystal and stirring was continued further to obtain a mixture. The mixture was charged in a 100 mL autoclave and subjected to a hydrothermal synthesis reaction at 160° C. for 4 days with stirring at 15 rpm under an autogenous pressure. The obtained product was filtrated, washed with water, and dried at 100° C. to obtain 0.98 g of a white powder. From the XRD pattern of the product (Table 4), it was confirmed that the obtained product was a CON zeolite. From the SEM image, the average primary particle diameter was 0.20 μm.

After removal of the organic structure-directing agent by calcination at 600° C. for 6 hours in an air stream, the $SiO_2/Al_2O_3$ ratio determined by $^{29}Si$-NMR was 32.

[Table 4]

TABLE 4

| 2θ (°) | d (Å) | Relative Intensity [I/Io × 100] |
|---|---|---|
| 7.74 | 11.41 | 100 |
| 8.35 | 10.58 | 15 |
| 8.96 | 9.86 | 27 |
| 13.14 | 6.73 | 16 |
| 14.14 | 6.26 | 10 |
| 15.17 | 5.84 | 16 |
| 15.63 | 5.67 | 13 |
| 16.67 | 5.31 | 7 |
| 18.04 | 4.91 | 8 |
| 19.56 | 4.54 | 21 |
| 20.20 | 4.39 | 53 |
| 21.27 | 4.17 | 25 |
| 21.90 | 4.06 | 46 |
| 22.86 | 3.89 | 59 |
| 23.83 | 3.73 | 11 |
| 24.20 | 3.68 | 11 |
| 25.07 | 3.55 | 13 |
| 26.46 | 3.37 | 30 |
| 27.66 | 3.22 | 8 |
| 27.96 | 3.19 | 9 |
| 28.59 | 3.12 | 12 |
| 28.90 | 3.09 | 11 |
| 29.59 | 3.02 | 8 |
| 30.25 | 2.95 | 9 |
| 30.78 | 2.90 | 7 |
| 31.43 | 2.84 | 8 |
| 31.84 | 2.81 | 8 |
| 33.13 | 2.70 | 8 |
| 35.25 | 2.54 | 8 |
| 35.65 | 2.52 | 7 |
| 36.82 | 2.44 | 7 |
| 37.17 | 2.42 | 7 |

Example A2

Firstly, 0.160 g of sodium hydroxide, 4.16 g of an aqueous solution of N,N,N-trimethyl-(−)-cis-myrtanylammonium hydroxide (30.8 mass %), and 4.33 g of water were mixed, to which 1.24 g of zeolite Y CBV 760 ($SiO_2/Al_2O_3$ ratio: 60, produced by Zeolyst International) was added, and the mixture was stirred for 2 hours. Further, 0.240 g of zeolite CIT-1 ($SiO_2/Al_2O_3$ ratio: 595, $SiO_2/B_2O$ ratio: 50) equivalent to 20 mass % with respect to the added $SiO_2$ was added as a seed crystal and stirring was continued further to obtain a mixture. The mixture was charged in a 100 mL autoclave, and subjected to a hydrothermal synthesis reaction at 160° C. for 4 days with stirring at 15 rpm under an autogenous pressure. The obtained product was filtrated, washed with water, and dried at 100° C. to obtain 0.86 g of a white powder. From the XRD pattern of the product, it was confirmed that the obtained product was a CON zeolite.

Example A3

A mixture was prepared and subjected to a hydrothermal synthesis reaction in the same manner and under the same conditions as in Example A2 except that 1.23 g of CBV 780 ($SiO_2/Al_2O_3$ ratio: 80, produced by Zeolyst International) was used as the zeolite Y. The post-treatment (filtration, washing with water, and drying) was carried out in the same manner as in Example A2 to obtain 0.71 g of a white powder. From the XRD pattern of the product, it was confirmed that the obtained product was a CON zeolite.

Example A4

Firstly, 0.198 g of potassium hydroxide, 1.39 g of an aqueous solution of N,N,N-trimethyl-(−)-cis-myrtanylammonium hydroxide (30.8 mass %), and 2.23 g of water were mixed, to which 0.510 of zeolite Y HSZ-360 HUA ($SiO_2$/$Al_2O_3$ ratio: 15, produced by Tosoh Corporation), and 0.492 g of colloidal silica SI-30 were added, and the mixture was stirred for 2 hours. Further, 0.120 g of zeolite CIT-1 ($SiO_2$/$Al_2O_3$ ratio: 595, $SiO_2$/$B_2O_3$ ratio: 50) equivalent to 20 mass % with respect to the added $SiO_2$ was added as a seed crystal and stirring was continued further to obtain a mixture. The mixture was charged in a 100 mL autoclave, and subjected to a hydrothermal synthesis reaction at 180° C. for 2 days with stirring at 15 rpm under an autogenous pressure. The obtained product was filtrated, washed with water, and dried at 100° C. to obtain 0.64 g of a white powder. From the XRD pattern of the product, it was confirmed that the obtained product was a CON zeolite.

Example A5

Firstly, 0.231 g of potassium hydroxide, 0.693 g of an aqueous solution of N,N,N-trimethyl-(−)-cis-myrtanylammonium hydroxide (30.8 mass %), and 1.69 g of water were mixed, to which 0.095 g of aluminum hydroxide (53.5 mass % in terms of aluminum oxide, produced by Sigma-Aldrich), and 1.97 g of colloidal silica SI-30 were added, and the mixture was stirred for 2 hours. Further, 0.120 g of zeolite CIT-1 ($SiO_2$/$Al_2O$ ratio: 595, $SiO_2$/$B_2O_3$ ratio: 50) equivalent to 20 mass % with respect to the added $SiO_2$ was added as a seed crystal, and stirring was continued further to obtain a mixture. The mixture was charged in a 100 mL autoclave, and subjected to a hydrothermal synthesis reaction at 180° C. for 4 days with stirring at 15 rpm under an autogenous pressure. The obtained product was filtrated, washed with water, and dried at 100° C. to obtain 0.72 g of a white powder. From the XRD pattern of the product, it was confirmed that the obtained product was a CON zeolite.

Example A6

A mixture was prepared and subjected to a hydrothermal synthesis reaction in the same manner and under the same conditions as in Example A5 except that 0.076 g of aluminum hydroxide was added. The post-treatment (filtration, washing with water, and drying) was carried out in the same manner as in Example A5 to obtain 0.66 g of a white powder. From the XRD pattern of the product, it was confirmed that the obtained product was a CON zeolite. From the SEM image, the average primary particle diameter was 0.10 μm.

Example A7

A mixture was prepared and subjected to a hydrothermal synthesis reaction in the same manner and under the same conditions as in Example A6 except that 0.060 g of zeolite CIT-1 ($SiO_2$/$Al_2O_3$ ratio: 595, $SiO_2$/$B_2O_3$ ratio: 50) equivalent to 10 mass % with respect to the added $SiO_2$ was added as a seed crystal. The post-treatment (filtration, washing with water, and drying) was carried out in the same manner as in Example A6 to obtain 0.61 g of a white powder. From the XRD pattern of the product, it was confirmed that the obtained product was a CON zeolite.

Example A8

A mixture was prepared and subjected to a hydrothermal synthesis reaction in the same manner and under the same conditions as in Example A6 except that 0.165 g of potassium hydroxide, 1.73 g of an aqueous solution of N,N,N-trimethyl-(−)-cis-myrtanylammonium hydroxide (30.8 mass %), and 0.985 g of water were added. The post-treatment (filtration, washing with water, and drying) was carried out in the same manner as in Example A6 to obtain 0.65 g of a white powder. From the XRD pattern of the product, it was confirmed that the obtained product was a CON zeolite.

Example A9

A mixture was prepared and subjected to a hydrothermal synthesis reaction in the same manner and under the same conditions as in Example A6 except that 0.198 g of potassium hydroxide, 1.39 g of an aqueous solution of N,N,N-trimethyl-(−)-cis-myrtanylammonium hydroxide (30.8 mass %), and 1.22 g g of water were added. The post-treatment (filtration, washing with water, and drying) was carried out in the same manner as in Example A6 to obtain 0.66 g of a white powder. From the XRD pattern of the product, it was confirmed that the obtained product was a CON zeolite.

Example A10

A mixture was prepared and subjected to a hydrothermal synthesis reaction in the same manner and under the same conditions as in Example A9 except that 0.060 g of zeolite CIT-1 ($SiO_2$/$Al_2O_3$ ratio: 595, $SiO_2$/$B_2O_3$ ratio: 50) equivalent to 10 mass % with respect to the added $SiO_2$ was added as a seed crystal. The post-treatment (filtration, washing with water, and drying) was carried out in the same manner as in Example A9 to obtain 0.56 g of a white powder. From the XRD pattern of the product, it was confirmed that the obtained product was a CON zeolite.

Example A11

A mixture was prepared and subjected to a hydrothermal synthesis reaction in the same manner and under the same conditions as in Example A6 except that 0.030 g of sodium hydroxide, 0.198 g of potassium hydroxide, 0.693 g of an aqueous solution of N,N,N-trimethyl-(−)-cis-myrtanylammonium hydroxide (30.8 mass %), and 1.70 g of water were added. The post-treatment (filtration, washing with water, and drying) was carried out in the same manner as in Example A6 to obtain 0.60 g of a white powder. From the XRD pattern of the product, it was confirmed that the obtained product was a CON zeolite.

Example A12

A mixture was prepared and subjected to a hydrothermal synthesis reaction in the same manner and under the same conditions as in Example A6 except that 0.165 g of potassium hydroxide, 0.088 g of cesium hydroxide (produced by Mitsuwa Chemicals Co., Ltd.), 1.39 g of an aqueous solution of N,N,N-trimethyl-(−)-cis-myrtanylammonium hydroxide (30.8 mass %), and 1.22 g of water were added. The post-treatment (filtration, washing with water, and drying) was carried out in the same manner as in Example A6 to obtain 0.67 g of a white powder. From the XRD pattern of the product, it was confirmed that the obtained product was a CON zeolite.

Example A13

Figure 7:
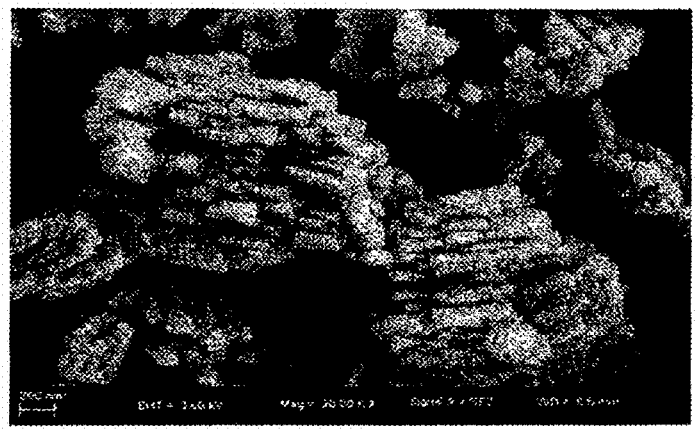
FIG. 7 is an SEM image of the CON zeolite obtained in Example A13.

A mixture was prepared and subjected to a hydrothermal synthesis reaction in the same manner and under the same conditions as in Example A5 except that 0.132 g of potassium hydroxide, 2.08 g of an aqueous solution of N,N,N-trimethyl-(−)-cis-myrtanylammonium hydroxide (30.8 mass %), 0.757 g of water, and 0.064 g of aluminum hydroxide were added. The post-treatment (filtration, washing with water, and drying) was carried out in the same manner as in Example A5 to obtain 0.62 g of a white powder. From the XRD pattern of the product, it was confirmed that the obtained product was a CON zeolite. From the SEM image (FIG. 7), the average primary particle diameter was 0.20 μm.

After removal of the organic structure-directing agent by calcination at 600° C. for 6 hours in an air stream, the $SiO_2/Al_2O_3$ ratio determined by $^{21}Si$-NMR was 29.

Example A14

A mixture was prepared and subjected to a hydrothermal synthesis reaction in the same manner and under the same conditions as in Example A5 except that 0.198 g of potassium hydroxide, 1.39 g of an aqueous solution of N,N,N-trimethyl-(−)-cis-myrtanylammonium hydroxide (30.8 mass %), 1.22 g of water, and 0.048 g of aluminum hydroxide were added. The post-treatment (filtration, washing with water, and drying) was carried out in the same manner as in Example A5 to obtain 0.51 g of a white powder. From the XRD pattern of the product, it was confirmed that the obtained product was a CON zeolite.

Example A15

A mixture was prepared and subjected to a hydrothermal synthesis reaction in the same manner and under the same conditions as in Example A14 except that 0.032 g of aluminum hydroxide was added. The post-treatment (filtration, washing with water, and drying) was carried out in the same manner as in Example A14 to obtain 0.47 g of a white powder. From the XRD pattern of the product, it was confirmed that the obtained product was a CON zeolite.

Example A16

A mixture was prepared and subjected to a hydrothermal synthesis reaction in the same manner and under the same conditions as in Example A6 except that 0.120 g of the zeolite Al-CIT-1 obtained in Example A8 was added. The post-treatment (filtration, washing with water, and drying) was carried out in the same manner as in Example A6 to obtain 0.65 g of a white powder. From the XRD pattern of the product, it was confirmed that the obtained product was a CON zeolite.

Example A17

A mixture was prepared and subjected to a hydrothermal synthesis reaction in the same manner and under the same conditions as in Example A6 except that 0.601 g of fumed silica AEROSIL 200 instead of the colloidal silica SI-30, and 3.03 g of water were added. The post-treatment (filtration, washing with water, and drying) was carried out in the same manner as in Example A6 to obtain 0.60 g of a white powder. From the XRD pattern of the product, it was confirmed that the obtained product was a CON zeolite.

Comparative Example A1

A mixture was prepared and subjected to a hydrothermal synthesis reaction in the same manner and under the same conditions as in Example A14 except that 0.010 g of aluminum hydroxide was added. The post-treatment (filtration, washing with water, and drying) was carried out in the same manner as in Example A14 to obtain 0.35 g of a white powder. From the XRD pattern of the product, it was confirmed that the obtained product was a mixed phase of a cristobalite phase and partly a CON phase.

The synthesis conditions and synthesis results of Examples A1 to A17 and Comparative Example A1 are shown in Table 5-1 or 5-2.
[Table 5]

TABLE 5-1

| | | Example A1 | Example A2 | Example A3 | Example A4 |
|---|---|---|---|---|---|
| Raw materials for synthesis | Silicon source Aluminum source | FAU zeolite (SAR30) Cataloid SI-30 FAU zeolite (SAR30) | FAU zeolite (SAR60) FAU zeolite (SAR60) | FAU zeolite (SAR80) FAU zeolite (SAR80) | FAU zeolite (SAR15) Cataloid SI-30 FAU zeolite (SAR15) |
| Feed molar ratio | Al/Si | 0.05 | 0.033 | 0.025 | 0.1 |
| | NaOH/Si | 0.2 | 0.2 | 0.2 | 0.02 |
| | KOH/Si | 0 | 0 | 0 | 0.3 |
| | Cs/Si | 0 | 0 | 0 | 0 |
| | SDA/Si | 0.3 | 0.3 | 0.3 | 0.2 |
| | $H_2O/Si$ | 20 | 20 | 20 | 20 |
| | Seed (mass %) | 20 | 20 | 20 | 20 |

TABLE 5-1-continued

| | | | | | |
|---|---|---|---|---|---|
| Hydrothermal synthesis conditions | Temperature (° C.) | 160 | 160 | 160 | 180 |
| | Time (day) | 4 | 4 | 4 | 2 |
| Synthesis results | Crystal phase | CON | CON | CON | CON |
| | Yield (%) | 66 | 58 | 48 | 83 |
| | Si/Al$_2$ ratio | 31 | 37 | 50 | 18 |
| | Si/B$_2$ ratio | 324 | 168 | 142 | 601 |
| | Acid content (mmol/g) | 1.1 | — | — | — |
| | Particle diameter (μm) | 0.2 | — | — | — |

| | | Example A5 | Example A6 | Example A7 | Example A8 | Example A9 |
|---|---|---|---|---|---|---|
| Raw materials for synthesis | Silicon source | Cataloid SI-30 | | | | |
| | Aluminum source | Al(OH)$_3$ | | | | |
| Feed molar ratio | Al/Si | 0.1 | 0.08 | 0.08 | 0.08 | 0.08 |
| | NaOH/Si | 0.02 | 0.02 | 0.02 | 0.02 | 0.02 |
| | KOH/Si | 0.35 | 0.35 | 0.35 | 0.25 | 0.3 |
| | Cs/Si | 0 | 0 | 0 | 0 | 0 |
| | SDA/Si | 0.1 | 0.1 | 0.1 | 0.25 | 0.2 |
| | H$_2$O/Si | 20 | 20 | 20 | 20 | 20 |
| | Seed (mass %) | 20 | 20 | 10 | 20 | 20 |
| Hydrothermal synthesis conditions | Temperature (° C.) | 180 | 180 | 180 | 180 | 180 |
| | Time (day) | 4 | 4 | 4 | 4 | 4 |
| Synthesis results | Crystal phase | CON | CON | CON | CON | CON |
| | Yield (%) | 93 | 87 | 87 | 86 | 87 |
| | Si/Al$_2$ ratio | 19 | 22 | 21 | — | — |
| | Si/B$_2$ ratio | 702 | 1111 | 1575 | — | — |
| | Acid content (mmol/g) | 0.75 | — | — | — | — |
| | Particle diameter (μm) | — | 0.1 | — | — | — |

TABLE 5-2

| | | Example A10 | Example A11 | Example A12 | Example A13 | Example A14 | Example A15 | Example A16 | Example A17 | Comparative Example A1 |
|---|---|---|---|---|---|---|---|---|---|---|
| Raw materials for synthesis | Silicon source | Cataloid SI-30 | | | | | | | Fumed Silica | Cataloid SI-30 |
| | Aluminum source | Al(OH)$_3$ | | | | | | | Al(OH)$_3$ | Al(OH)$_3$ |
| Feed molar ratio | Al/Si | 80 | 80 | 0.08 | 0.067 | 0.05 | 0.033 | 0.08 | 0.08 | 0.01 |
| | NaOH/Si | 2 | 0.1 | 0.02 | 0.02 | 0.02 | 0.02 | 0.02 | 0.02 | 0.02 |
| | KOH/Si | 0.3 | 0.3 | 0.25 | 0.2 | 0.3 | 0.3 | 0.35 | 0.35 | 0.3 |
| | Cs/Si | 0 | 0 | 0.05 | 0 | 0 | 0 | 0 | 0 | 0 |
| | SDA/Si | 0.2 | 0.1 | 0.2 | 0.3 | 0.2 | 0.2 | 0.1 | 0.1 | 0.2 |
| | H$_2$O/Si | 20 | 20 | 20 | 20 | 20 | 20 | 20 | 20 | 20 |
| | Seed (mass %) | 10 | 20 | 20 | 20 | 20 | 20 | 20 | 20 | 20 |
| Hydrothermal synthesis conditions | Temperature (° C.) | 180 | 180 | 180 | 180 | 180 | 180 | 180 | 180 | 180 |
| | Time (day) | 4 | 4 | 4 | 4 | 4 | 4 | 4 | 4 | 4 |
| Synthesis results | Crystal phase | CON | CON | CON | CON | CON | CON | CON | CON | Cristobalite + CON |
| | Yield (%) | 80 | 79 | 88 | 82 | 68 | 64 | 85 | 79 | 48 |
| | Si/Al$_2$ ratio | 21 | 22 | 23 | 26 | 31 | — | — | 22 | — |
| | Si/B$_2$ ratio | 1389 | 897 | 2861 | 781 | 442 | — | — | 1626 | — |
| | Acid content (mmol/g) | — | — | — | — | — | — | — | — | — |
| | Particle diameter (μm) | — | — | — | 0.16 | — | — | — | — | — |

The details of the raw materials used for the syntheses in Examples A1 to A17, and Comparative Example A1 are as follows. NaOH (produced by Kishida Chemical Co., Ltd.), KOH (produced by Kishida Chemical Co., Ltd.), CsOH (produced by Mitsuwa Chemicals Co., Ltd.), and Cataloid SI-30 (silica concentration: 30.6 weight %, produced by JGC Catalysts and Chemicals Ltd.)

A yield (weight %) was calculated according to the following formula.

(Yield)=(Weight of CON zeolite including SDA (g))/[(Weight (g) of silicon raw material and aluminum raw material added during production in terms of $SiO_2$ and $Al_2O_3$ respectively)+(Weight (g) of seed crystal zeolite)]×100

(Evaluation of Performance of Hydrocarbon Trapping Material)

In order to examine the adsorption characteristics of a CON zeolite of the present embodiment, desorbed toluene was detected by a mass spectrometer based on temperature-programmed desorption (TPD) of toluene. Approximately 100 mg of a zeolite sample was weighed on to a Pt boat, which was placed in a quartz tube, heated to 300° C. at 20° C./min in a helium stream of 50 cc/min, and allowed to stand there for 2 hours to remove adsorbed water from zeolite. After cooling down to 50° C. the system was evacuate with a rotary pump (RP) and a turbo molecular pump (TMP). Next, toluene was introduced into a quartz tube in a vacuum state at 50° C. to be adsorbed for 15 min. Thereafter, as a pre-desorption treatment, the temperature was raised to 90° C. at 10° C./min in a helium stream of 50 cc/min, and kept there for 10 min (pre-desorption treatment step). Toluene temperature-programmed desorption was measured after heating a sample from 90° C. up to 390° C. at 20° C./min in a helium stream of 50 cc/min, and allowing it to stand there for 10 min, by detecting the toluene freed in the course of the program with a mass spectrometer. The toluene adsorption amount was calculated as follows. Since a water component was also detected together with toluene in performing temperature-programmed desorption, a conversion factor for calculating a water desorption amount was determined from the area of the m/z=18 peak in a mass spectrometry of calcium oxalate ($CaC_2O_4 \cdot H_2O$) as a reference substance. Further, a reference sample, on which toluene was adsorbed, was prepared, and the TG-DTA loss in the range of 90° C. to 390° C. was measured. Such portion of the loss as exceeds the water desorption amount determined from the area of the m/z=18 peak in the temperature-programmed desorption is deemed as the toluene desorption amount, and a conversion factor for obtaining a toluene desorption amount was calculated from the area of peak of the m/z=91 peak. Using such conversion factors, the desorbed amount of toluene at the time of temperature rise of a CON zeolite was calculated.

Example A18

Figure 8:
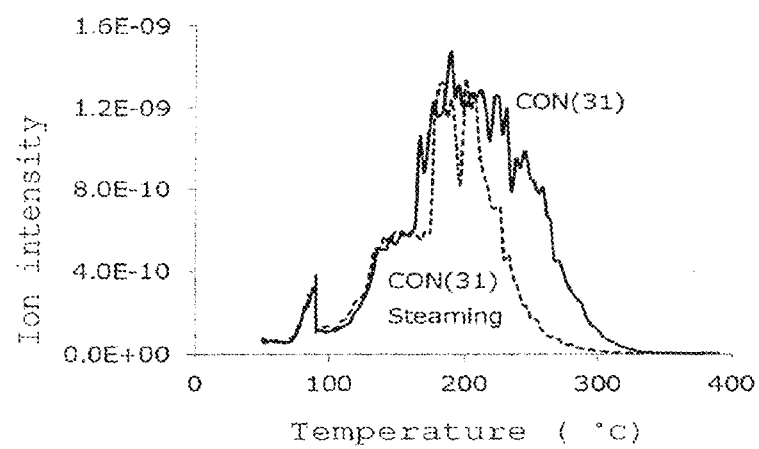
FIG. 8 is a temperature-programmed desorption profile of toluene with respect to the CON zeolite according to Example A18.

The CON zeolite ($Si/Al_2$=31) obtained in Example A1 was calcined at 600° C. for 6 hours in an air stream to obtain a Na type CON zeolite. Next, the zeolite was subjected to ion exchange twice with a 1 M aqueous solution of ammonium nitrate at 80° C. for 1 hour, dried at 100° C., and then calcined at 500° C. for 6 hours in an air stream to obtain a protonic CON zeolite. The total acid content determined by $NH_3$-TPD was 1.1 mmol/g. An evaluation of the adsorption performance as a hydrocarbon trapping material was carried out by the above toluene temperature-programmed desorption measurement. Furthermore, in order to evaluate the hydrothermal stability, a steam treatment was conducted at 800° C. and $H_2O$/Air=10/90 vol % for 5 hours, and then a toluene temperature-programmed desorption measurement was similarly carried out. The results are shown in Table 6 and FIG. 8.

Comparative Example A2

Figure 9:
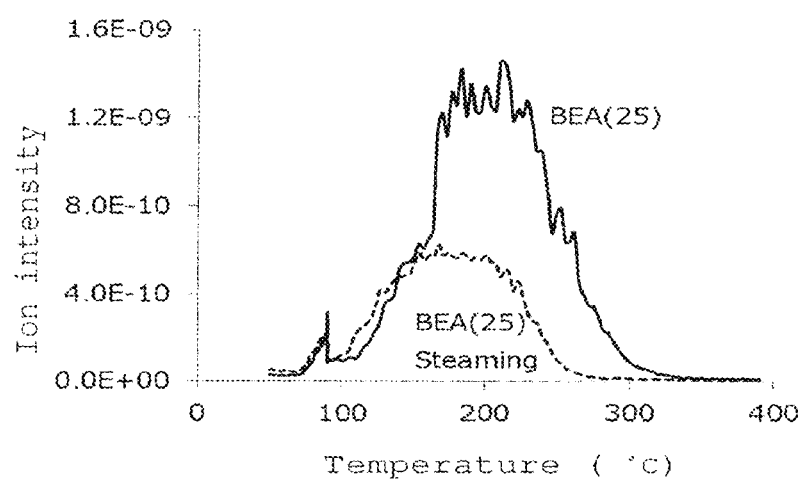
FIG. 9 is a temperature-programmed desorption profile of toluene with respect to the BEA zeolite according to Comparative Example A2.

With respect to a protonic BEA zeolite ($Si/Al_2$=25, Reference Catalyst of Catalysis Society of Japan, JRC-Z-HB25), toluene temperature-programmed desorption measurements were conducted identically with Example A18 before and after the steam treatment. The results are shown in Table 6 and FIG. 9.

Example A19

Figure 10:
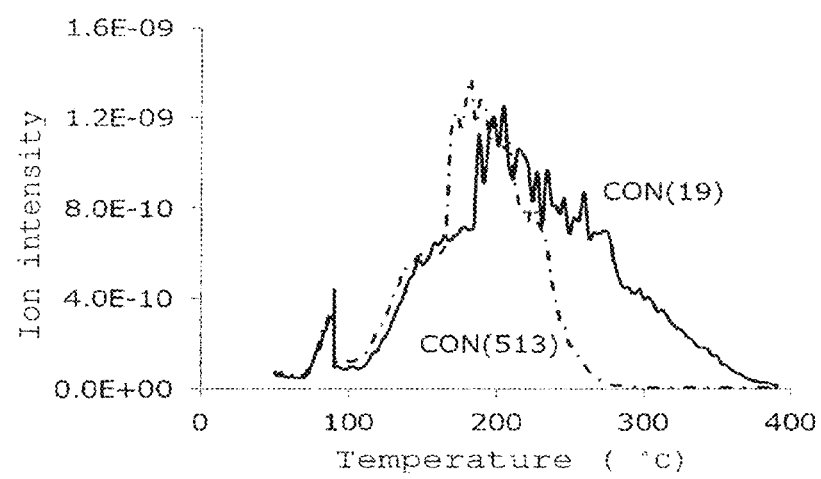
FIG. 10 is temperature-programmed desorption profiles of toluene with respect to the CON zeolites according to Example A19 and Comparative Example A3.

The CON zeolite ($Si/Al_2$=19) obtained in Example A5 was treated identically with Example A18 to obtain a protonic CON zeolite. The total acid content determined by $NH_3$-TPD was 0.75 mmol/g. An evaluation of the performance as a hydrocarbon trapping material was carried out by a toluene temperature programmed-desorption measurement as described above. The results are shown in Table 6 and FIG. 10.

Comparative Example A3

A hydrothermal synthesis was carried out with the same composition and synthesis conditions as Preparation Example A to prepare [B,Al]-CIT-1 ($Si/Al_2$=513, and $Si/B_2$=48), which was treated in the same manner as in Example A18 to obtain a protonic CON zeolite. An evaluation of the performance as a hydrocarbon trapping material was carried out by a toluene temperature-programmed desorption measurement as described above. The results are shown in Table 6 and FIG. 10.

[Table 6]

TABLE 6

| | Zeolite | Before/After Steam treatment | Toluene desorption amount (mmol/g) | Desorption end temperature (° C.) |
|---|---|---|---|---|
| Example A18 | CON zeolite ($Si/Al_2$ = 31) | Before | 2.2 | 330 |
| | | After | 1.4 | 296 |
| Comparative Example A2 | BEA zeolite ($Si/Al_2$ = 25) | Before | 2.1 | 330 |
| | | After | 1.0 | 290 |
| Example A19 | CON zeolite ($Si/Al_2$ = 19) | Before | 1.9 | 390 |
| Comparative Example A3 | CON zeolite ($Si/Al_2$ = 513) | Before | 1.7 | 280 |

In Example A18, the CON zeolite with $Si/Al_2$=31 exhibited a toluene desorption amount (hereinafter referred to as "adsorption amount") of 2.2 mmol/g in the fresh state (before a steam treatment), and 1.4 mmol/g after a steam treatment. On the other hand, in Comparative Example A2, the BEA zeolite with $Si/Al_2$=25 exhibited a toluene adsorption amount of 2.1 mmol/g in the fresh state and 1.0 mmol/g after a steam treatment. When the toluene adsorption amounts before and after the steam treatment were compared, in Comparative Example A2 it decreased to 48%, while in Example A18, it secured 64%. This indicates that the CON zeolite of Example A18 has higher steam stability compared to the BEA type zeolite exhibiting an equivalent toluene adsorption amount.

Meanwhile, in Example A19, the CON zeolite with Si/Al$_2$=19 exhibited a toluene adsorption amount of 1.9 mmol/g and a desorption end temperature of 390° C. in the fresh state. On the other hand, the CON zeolite having Si/Al$_2$=513 in Comparative Example A3 prepared by a publicly known method exhibited a toluene adsorption amount of 1.7 mmol/g and a desorption end temperature of 280° C. When the toluene adsorption amounts and the desorption end temperatures are compared, it becomes clear that the CON zeolites of Examples A18 and A19 exhibit a higher toluene adsorption amount as well as a higher desorption end temperature.

As obvious from the above results, a CON zeolite of the present embodiment exhibits a high adsorption amount and high steam stability, therefore it may be favorably used as an adsorbent, particularly as an adsorbent for a hydrocarbon component (such as an automobile hydrocarbon trapping material). Further, since the CON zeolite of the present embodiment has a high acid content and high steam stability, it is believed to be also applicable to an exhaust gas treatment catalyst required to have high acid content and high steam stability similarly to the adsorbent.

INDUSTRIAL APPLICABILITY

A zeolite catalyst according to the present invention may be applicable to a catalyst for producing selectively a lower olefin, such as propylene and butene, from a raw material containing methanol and/or dimethyl ether.

While the invention has been described in detail and with reference to specific embodiments thereof, it will be apparent to one skilled in the art that various changes and modifications can be made therein without departing from the spirit and scope thereof.

The invention claimed is:

1. A CON zeolite wherein, silicon and aluminum are present in a molar ratio of aluminum to silicon of 0.04 or more and 0.30 or less and the framework is CON as per the code specified by the international Zeolite Association (IZA), wherein the CON zeolite consists essentially of a crystal of polymorph B and the CON zeolite has an average particle diameter of 1 μm or less,
wherein the CON zeolite is obtained by hydrothermal synthesis of a mixture comprising a silicon source, an aluminum source, an alkali metal element source and/or an alkaline earth metal element source, an organic structure-directing agent comprising N,N,N-trimethyl-(−)-cis-myrtanylammonium cation and/or N,N,N-trimethyl-(+)-cis-myrtanylammonium cation, and water, wherein the molar ratio of aluminum to silicon in the mixture is higher than 0.01, the molar ratio of the sum of an alkali metal and alkaline earth metal to silicon in the mixture is 0.20 or more.

2. A method of producing a zeolite of the type CON as per the code specified by the International Zeolite Association (IZA) by hydrothermal synthesis of a mixture comprising a silicon source, an aluminum source, an alkali metal element source and/or an alkaline earth metal element source, an organic structure-directing agent comprising N,N,N-trimethyl-(−)-cis-myrtanylammonium cation and/or N,N,N-trimethyl-(+)-cis-myrtanylammonium cation, and water, wherein the molar ratio of aluminum to silicon in the mixture is higher than 0.01, the molar ratio of the sum of an alkali metal and alkaline earth metal to silicon in the mixture is 0.20 or more.

3. The method of producing a CON zeolite according to claim 2, wherein the molar ratio of aluminum to silicon in the mixture is 0.08 or more.

4. A CON zeolite obtained by the method of according to claim 2.

5. A catalyst for producing a lower olefin or an aromatic hydrocarbon containing the CON zeolite according to claim 1.

6. A catalyst for producing a lower olefin or an aromatic hydrocarbon containing the CON zeolite according to claim 4.

7. An adsorbent containing the CON zeolite according to claim 1.

8. An adsorbent containing the CON zeolite according to claim 4.

9. An exhaust gas treatment catalyst containing the CON zeolite according to claim 1.

10. An exhaust gas treatment catalyst containing the CON zeolite according to claim 4.

11. The CON zeolite according to claim 1, further comprising boron and wherein a molar ratio of boron to silicon is 0.00002 or more.

* * * * *